(12) United States Patent  
Lipowski et al.

(10) Patent No.: US 11,559,318 B2  
(45) Date of Patent: Jan. 24, 2023

(54) RADIALLY-FIRING ELECTROHYDRAULIC LITHOTRIPSY PROBE

(71) Applicant: Northgate Technologies Inc., Elgin, IL (US)

(72) Inventors: Stan J. Lipowski, Loves Park, IL (US); Robert Mantell, Arlington Heights, IL (US); Chuck Zander, McHenry, IL (US)

(73) Assignee: NORTHGATE TECHNOLOGIES INC., Elgin, IL (US)

(*) Notice: Subject to any disclaimer, the term of this patent is extended or adjusted under 35 U.S.C. 154(b) by 611 days.

(21) Appl. No.: 16/541,475

(22) Filed: Aug. 15, 2019

(65) Prior Publication Data

US 2020/0038044 A1   Feb. 6, 2020

Related U.S. Application Data

(63) Continuation of application No. 14/966,899, filed on Dec. 11, 2015, now Pat. No. 10,426,500, which is a (Continued)

(51) Int. Cl.
*A61B 17/22* (2006.01)
*A61B 18/00* (2006.01)
(Continued)

(52) U.S. Cl.
CPC ........ *A61B 17/22022* (2013.01); *G10K 15/06* (2013.01); *A61B 2017/0023* (2013.01); (Continued)

(58) Field of Classification Search
CPC ............ A61B 17/22022; A61B 17/225; A61B 17/22004; A61B 17/22; A61B 2017/22098; A61B 2017/22025
See application file for complete search history.

(56) References Cited

U.S. PATENT DOCUMENTS

| 3,785,382 A | 1/1974 | Schmidt-Kloiber et al. |
| 3,902,499 A | 9/1975 | Shene |

(Continued)

FOREIGN PATENT DOCUMENTS

| CN | 101043914 A | 5/1982 |
| DE | 3038445 A1 | 5/1992 |

(Continued)

OTHER PUBLICATIONS

Rosenchein, et al., "Shock-Wave Thrombus Ablation, a New Method for Noninvasive Mechanical Thrombolysis", The American Journal of Cardiology, vol. 70, Nov. 15, 1992, pp. 1358-1361.

(Continued)

*Primary Examiner* — Anh T Dang  
(74) *Attorney, Agent, or Firm* — Crowell & Moring, L.L.P.

(57) ABSTRACT

An invasive electrohydraulic lithotripter probe may comprise a lithotripter tip that comprises a first electrode and a second electrode. The lithotripter tip has a length in excess of 250 cm and is dimensioned to be inserted into a long channel having a length in excess of 250 cm. The lithotripter probe may include a material that reinforces a linear strength of at least a portion of the lithotripter probe.

10 Claims, 17 Drawing Sheets

Related U.S. Application Data continuation of application No. 13/302,706, filed on Nov. 22, 2011, now Pat. No. 9,579,114, which is a continuation of application No. 12/436,547, filed on May 6, 2009, now abandoned.

(60) Provisional application No. 61/051,262, filed on May 7, 2008.

(51) Int. Cl.
*G10K 15/06* (2006.01)
*A61B 90/00* (2016.01)
*A61B 17/00* (2006.01)

(52) U.S. Cl.
CPC ........... *A61B 2017/00734* (2013.01); *A61B 2017/22025* (2013.01); *A61B 2017/22098* (2013.01); *A61B 2018/00988* (2013.01); *A61B 2090/0803* (2016.02); *A61B 2090/0814* (2016.02)

(56) References Cited

U.S. PATENT DOCUMENTS

| | | | |
|---|---|---|---|
| 4,027,674 A * | 6/1977 | Tessler | A61B 17/22022 606/128 |
| 4,608,983 A | 9/1986 | Muller et al. | |
| 4,610,249 A | 9/1986 | Makofski et al. | |
| 4,662,126 A | 5/1987 | Malcolm | |
| 4,685,458 A | 8/1987 | Leckrone | |
| 4,905,673 A | 3/1990 | Pimiskern | |
| 4,927,427 A | 5/1990 | Kriauciunas et al. | |
| 4,955,143 A | 9/1990 | Haqelauer | |
| 4,966,132 A | 10/1990 | Nowacki et al. | |
| 5,009,232 A | 4/1991 | Hassler et al. | |
| 5,044,354 A | 9/1991 | Goldhorn et al. | |
| 5,046,503 A | 9/1991 | Schneiderman | |
| 5,047,685 A | 9/1991 | Nowacki et al. | |
| 5,057,103 A | 10/1991 | Davis | |
| 5,065,762 A | 11/1991 | Ifflaender et al. | |
| 5,072,733 A | 12/1991 | Spector et al. | |
| 5,078,717 A | 1/1992 | Parins et al. | |
| 5,102,402 A | 4/1992 | Dror et al. | |
| 5,152,767 A | 10/1992 | Sypal et al. | |
| 5,152,768 A | 10/1992 | Bhatta | |
| 5,154,722 A | 10/1992 | Filip et al. | |
| 5,160,336 A | 11/1992 | Favre | |
| 5,174,280 A | 12/1992 | Gruenwald et al. | |
| 5,176,675 A | 1/1993 | Watson et al. | |
| 5,178,136 A | 1/1993 | Wess et al. | |
| 5,195,508 A | 3/1993 | Muller et al. | |
| 5,246,447 A | 9/1993 | Rosen et al. | |
| 5,281,231 A | 1/1994 | Rosen et al. | |
| 5,295,958 A | 3/1994 | Shturman | |
| 5,324,255 A | 6/1994 | Passafaro et al. | |
| 5,368,591 A | 11/1994 | Lennox et al. | |
| 5,395,335 A | 3/1995 | Jang | |
| 5,400,267 A | 3/1995 | Denen et al. | |
| 5,417,208 A | 5/1995 | Winkler | |
| 5,420,473 A | 5/1995 | Thomas | |
| 5,420,743 A | 5/1995 | Thomas | |
| 5,425,735 A | 6/1995 | Rosen et al. | |
| 5,472,406 A | 12/1995 | de la Torre et al. | |
| 5,603,731 A | 2/1997 | Whitney | |
| 5,609,606 A | 3/1997 | O'Boyle | |
| 5,662,590 A | 9/1997 | de la Torre et al. | |
| 5,700,243 A | 12/1997 | Narciso | |
| 5,722,980 A | 3/1998 | Schulz et al. | |
| 5,741,272 A | 4/1998 | Kuhne | |
| 5,766,168 A | 6/1998 | Mantell | |
| 5,782,829 A | 7/1998 | Swiantek et al. | |
| 5,836,898 A | 11/1998 | Schwieker | |
| 5,846,218 A | 12/1998 | Brisken et al. | |
| 5,893,840 A | 4/1999 | Hull et al. | |
| 6,033,371 A | 3/2000 | Torre et al. | |
| 6,083,232 A | 7/2000 | Cox | |
| 6,113,560 A | 9/2000 | Simnacher | |
| 6,146,358 A | 11/2000 | Rowe | |
| 6,186,963 B1 | 2/2001 | Schwarze et al. | |
| 6,193,715 B1 * | 2/2001 | Wrublewski | A61B 18/1402 606/49 |
| 6,210,408 B1 | 4/2001 | Chandrasekaran et al. | |
| 6,217,531 B1 | 4/2001 | Reitmajer | |
| 6,217,588 B1 | 4/2001 | Jerger et al. | |
| 6,261,298 B1 | 7/2001 | Irion et al. | |
| 6,277,138 B1 | 8/2001 | Levinson et al. | |
| 6,287,272 B1 | 9/2001 | Brisken et al. | |
| 6,312,434 B1 | 11/2001 | Sutrina et al. | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | de la Torre et al. | |
| 6,440,061 B1 | 8/2002 | Wenner et al. | |
| 6,440,123 B1 | 8/2002 | Engel | |
| 6,511,485 B2 | 1/2003 | Hirt et al. | |
| 6,514,203 B2 | 2/2003 | Bukshpan | |
| 6,520,968 B2 | 2/2003 | Bates et al. | |
| 6,524,251 B2 | 2/2003 | Rabiner et al. | |
| 6,533,792 B2 | 3/2003 | Menne et al. | |
| 6,558,397 B2 | 5/2003 | Hirt et al. | |
| 6,572,733 B1 | 6/2003 | Banerjee | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 | 11/2003 | Rabiner et al. | |
| 6,689,089 B1 | 2/2004 | Tiedtke et al. | |
| 6,689,122 B2 | 2/2004 | Yamamota | |
| 6,736,784 B1 | 5/2004 | Menne et al. | |
| 6,740,081 B2 | 5/2004 | Hilal | |
| 6,740,096 B2 | 5/2004 | Teague et al. | |
| 6,755,821 B1 | 6/2004 | Fry | |
| 6,758,842 B2 | 7/2004 | Irion et al. | |
| 6,770,039 B2 | 8/2004 | Zhong et al. | |
| 6,780,161 B2 | 8/2004 | Faragalla et al. | |
| 6,939,320 B2 | 9/2005 | Lennox | |
| 6,989,009 B2 | 1/2006 | Lafontaine | |
| 7,066,904 B2 | 6/2006 | Rosenthal et al. | |
| 7,101,380 B2 | 9/2006 | Khachin et al. | |
| 7,241,295 B2 | 7/2007 | Maguire | |
| 7,569,032 B2 | 8/2009 | Naimark et al. | |
| 2002/0177889 A1 | 11/2002 | Brisken et al. | |
| 2003/0004434 A1 | 1/2003 | Greco et al. | |
| 2003/0135223 A1 * | 7/2003 | Teague | A61B 17/221 606/127 |
| 2003/0163081 A1 | 8/2003 | Constantz et al. | |
| 2003/0176769 A1 | 9/2003 | Soble et al. | |
| 2003/0229370 A1 | 12/2003 | Miller | |
| 2004/0044308 A1 | 3/2004 | Naimark et al. | |
| 2004/0082859 A1 | 4/2004 | Schaer | |
| 2004/0097996 A1 | 5/2004 | Rabiner et al. | |
| 2004/0249401 A1 | 12/2004 | Rabiner et al. | |
| 2004/0254570 A1 | 12/2004 | Hadjicostis et al. | |
| 2005/0015953 A1 | 1/2005 | Keidar | |
| 2005/0021013 A1 | 1/2005 | Visuri et al. | |
| 2005/0090846 A1 | 4/2005 | Pederson et al. | |
| 2005/0113815 A1 | 5/2005 | Ritchie et al. | |
| 2005/0171527 A1 | 8/2005 | Bhola | |
| 2005/0245866 A1 | 11/2005 | Azizi | |
| 2006/0004286 A1 | 1/2006 | Chang et al. | |
| 2006/0074484 A1 | 4/2006 | Huber | |
| 2006/0078265 A1 | 4/2006 | Loeb | |
| 2006/0190022 A1 | 8/2006 | Beyar et al. | |
| 2006/0264904 A1 * | 11/2006 | Kerby | A61M 25/0021 604/523 |
| 2007/0016112 A1 * | 1/2007 | Schultheiss | A61B 17/22004 601/4 |
| 2007/0123851 A1 | 5/2007 | Alejandro et al. | |
| 2007/0129667 A1 | 6/2007 | Tiedtke et al. | |
| 2007/0239082 A1 | 10/2007 | Schultheiss et al. | |
| 2007/0239253 A1 | 10/2007 | Jagger et al. | |
| 2007/0244423 A1 | 10/2007 | Zummeris et al. | |
| 2007/0299481 A1 | 12/2007 | Syed et al. | |
| 2008/0077165 A1 | 3/2008 | Murphy | |
| 2008/0097251 A1 | 4/2008 | Babaev | |

(56) References Cited

U.S. PATENT DOCUMENTS

| | | |
|---|---|---|
| 2008/0247508 A1 | 10/2008 | Harrington et al. |
| 2009/0254114 A1 | 10/2009 | Hirszowics et al. |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0044596 A1 | 2/2010 | Ishikawa |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0305565 A1 | 12/2010 | Truckai et al. |
| 2010/0324554 A1 | 12/2010 | Giffard et al. |
| 2011/0118634 A1 | 5/2011 | Golan |
| 2011/0166570 A1 | 7/2011 | Hawkins et al. |
| 2011/0295227 A1 | 12/2011 | Hawkins et al. |
| 2012/0071889 A1 | 3/2012 | Mantell et al. |
| 2012/0116289 A1 | 5/2012 | Hawkins et al. |
| 2012/0203255 A1 | 8/2012 | Hawkins et al. |
| 2012/0221013 A1 | 8/2012 | Hawkins et al. |
| 2013/0030431 A1 | 1/2013 | Adams |
| 2013/0030447 A1 | 1/2013 | Adams |
| 2013/0116714 A1 | 5/2013 | Adams et al. |

FOREIGN PATENT DOCUMENTS

| | | |
|---|---|---|
| EP | 0442199 A1 | 8/1991 |
| EP | 571306 A1 | 11/1993 |
| JP | 07047135 A | 2/1985 |
| JP | 62275446 A | 11/1987 |
| JP | 03063059 A | 3/1991 |
| JP | 06125915 A | 5/1994 |
| JP | 10099444 A | 4/1998 |
| JP | 10314177 A | 12/1998 |
| JP | 2002538932 A | 11/2002 |
| JP | 2004357792 A | 12/2004 |
| JP | 2005515825 A | 6/2005 |
| JP | 2006516465 A | 7/2005 |
| JP | 2008506447 A | 3/2008 |
| JP | 2011528963 A | 12/2011 |
| WO | 2004/069072 A2 | 8/2004 |
| WO | 2006/006169 A2 | 1/2006 |
| WO | 2006/127158 A2 | 11/2006 |
| WO | 2007/088546 A2 | 8/2007 |
| WO | 2007/149905 A2 | 12/2007 |
| WO | 2009/121017 A1 | 10/2009 |
| WO | 2009/152352 A2 | 12/2009 |
| WO | 2010/014515 | 2/2010 |
| WO | 2011/069025 A1 | 6/2011 |
| WO | 2011/143468 A2 | 11/2011 |
| WO | 2013/070750 A1 | 5/2013 |

OTHER PUBLICATIONS

Zhong. et al., "Transient Oscillation of Cavitation Bubbles Near Stone Surface During Electrohydraulic Lithotripsy", Journal of Endourology, vol. 11, No. 1, Feb. 1997, pp. 55-61.
U.S. Appl. No. 61/061,170, filed Jun. 13, 2008 (EXPIRED).
International Search Report dated Jan. 19, 2010, for International Patent Application No. PCT/US2009/047070, 4 pages.
International Search Report dated Jun. 11, 2010, for International Patent Application No. PCT/US2009/063354, 3 pages.
International Search Report dated Apr. 21, 2010, for International Application No. PCT/IB09/05519.
Written Opinion of the International Searching Authority dated Apr. 21, 2010, for International Application No. PCT/IB09/05519.
http://www.as.miami.edu/chemistry/2086/Chapter_21_class_part1.htm, Chapter 21: Blood Vessels and Circulation, p. 3 of 10.
McCall, Ruth and Tankersley, Cathee, "Phlebotomy Essentials 4$^{th}$ edition", Copyright 2008 Lippincott Williams and Wilkins, p. 188.
Walker, Richard, "Guide to the Human Body", Copyright 2004 Firefly Books Ltd., p. 68.

* cited by examiner

RADIALLY-FIRING ELECTROHYDRAULIC LITHOTRIPSY PROBE

RELATED APPLICATIONS

The present application is a continuation of U.S. patent application Ser. No. 14/966,899 (still pending), filed on Dec. 11, 2015, which is a continuation of U.S. patent application Ser. No. 13/302,706, filed Nov. 22, 2011 (now U.S. Pat. No. 9,579,114, issued Feb. 28, 2017), which is a continuation of U.S. patent application Ser. No. 12/436,547 (abandoned), filed May 6, 2009, which claims priority to U.S. Provisional Patent Appln. No. 61/051,262, filed May 7, 2008, the entirety of each of which are hereby incorporated by reference.

BACKGROUND

Electrohyrdaulic lithotripsy has been used in the medical field, primarily for breaking concretions in the urinary or biliary track. Conventional lithotripsy probes produce a shockwave that radiates axially from a distal end of the lithotripsy probe. While a shockwave radiating axially from a distal end of a lithotripsy probe is useful in breaking up concretions such as a kidney stone, it is often difficult to use these types of probes to break up annular concretions, such as concretions around a heart valve. Accordingly, improved lithotripsy probes are desirable for breaking up concretions that are not located axially from a distal end of a lithotripsy probe.

DETAILED DESCRIPTION OF THE DRAWINGS

The present disclosure is directed to an invasive radially-firing electrohydraulic lithotripsy probe that creates a substantially annular shockwave for uses such as breaking up concretions that are at least semi-annular or disrupting tissue of a body organ. Generally, embodiments of the disclosed radially-firing electrohydraulic lithotripsy ("EHL") probes include a first electrode at a distal end of the probe, and a second electrode coaxially aligned with the first electrode. A difference in voltage polarities between the first and second electrodes causes an electric arc, resulting in a shockwave that is at least semi-annular that radiates radially from the lithotripsy probe.

In one implementation, the EHL probes described below may be delivered to a proper channel of a heart by threading (or pre-loading) an EHL probe through a center lumen of a catheter or balloon device. The catheter may be threaded through appropriate veins or arteries to address concretions either forming in vessels or even in the valves of the heart or other organs.

In other implementations, the EHL probes described below may be delivered to a small lumen of a body organ for the purpose of disturbing or disrupting (distressing) tissue of the body organ in such a way as to cause a stricture or a "scarring" of the tissue for the purpose of creating a permanent stricture or blockage of the lumen. For example, the EHL probes described below may be used to purposely create a blockage in a fallopian tube for the purpose of preventing pregnancies (sterilization). A fallopian tube, which is approximately 1 mm in diameter, would have one of the EHL probes described below threaded into it. The EHL probe may be threaded through the fallopian tube(s) to address the inner surface of the fallopian tube. Upon generating the EHL spark and subsequent pressure wave in a radial manner, a rupturing or disrupting of the walls of the inner surface of the fallopian tube can be accomplished. The subsequent healing or scarring of the walls cause the walls of the inner surface of the fallopian tube to knit together and create a blockage that renders the fallopian tube non-functional, thereby sterilizing a patient and preventing pregnancies.

Figure 1:
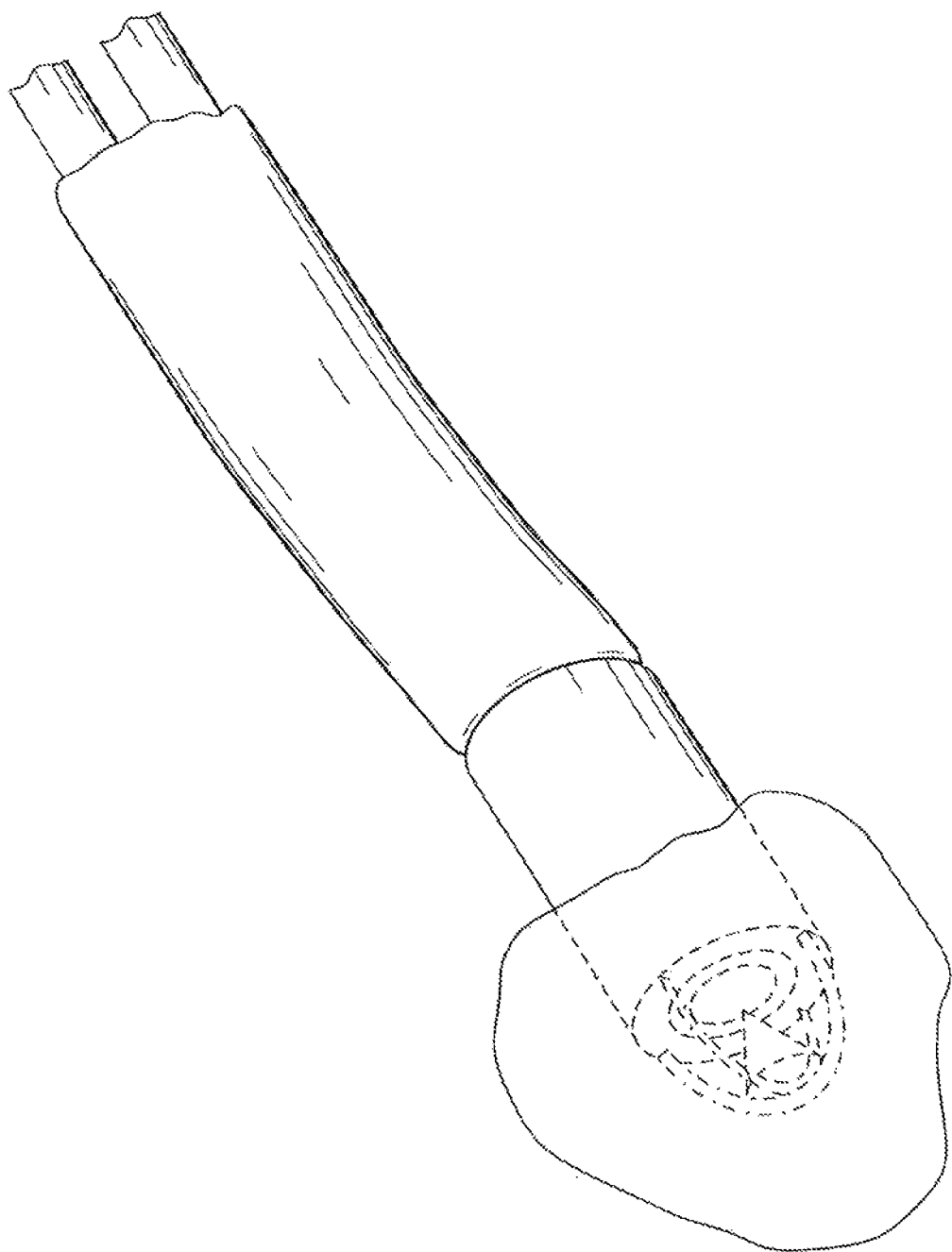
FIG. 1 is a perspective view of one embodiment of a radially-firing electrohydraulic lithotripsy probe.
Figure 2:
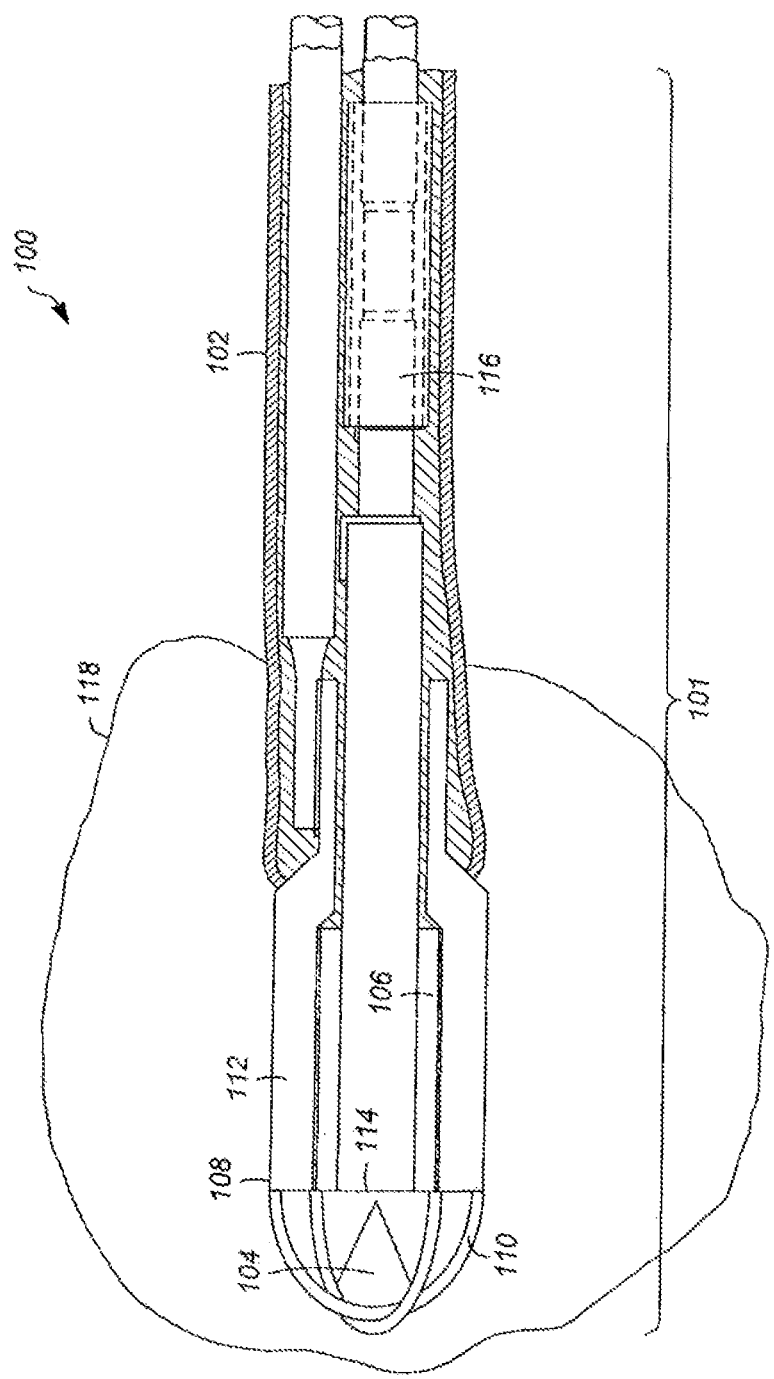
FIG. 2 is a cross-sectional side view of the radially-firing electrohydraulic lithotripsy probe of FIG. 1.

Referring to FIGS. 1 and 2, one embodiment of a radially-firing EHL probe 100 (the "probe 100") includes a lithotripsy probe tip 101 including an insulating body 102, a first electrode 104, and a second electrode 106. Typically, the first electrode 104 is positioned at a first distal end 108 of the lithotripsy probe tip 101. In one implementation, the first electrode 106 is conic in shape and includes an electrically conductive material such as copper, silver, or stainless steels. However, the first electrode 106 may be other shapes such as a curved surface and/or made of other electrically conductive material.

The first electrode 104 is supported by a plurality of wires 110 extending from the first distal end 108 of the lithotripsy probe tip 101. The plurality of wires 110 are made of an electrically conductive material, such as copper, silver, stainless steel, or other conductive materials, and electrically coupled with a first electrically conductive structure 112 in the EHL probe 100. Typically, the plurality of wires 110 are insulated other than where the plurality of wires 110 are electrically coupled with the first electrode 104 and the first electrically conductive structure 112. As known in the art, the first conductive structure 112 may be coupled with an electrical source, such as an electrohydraulic generator (Autolith, Supplied by Norhgate Technologies Inc.), used to charge the first electrode 104 to a first polarity.

The second electrode 106 is positioned in the body of the lithotripsy probe tip 101. In one implementation, at least an end 114 of the second electrode 106 is cylindrical and includes an electrically conductive material such as copper, silver, stainless steel, or other conductive materials. However, the second electrode 106 may be other shapes. The second electrode 106 is positioned in the lithotripsy probe tip 101 such that the second electrode 106 is coaxially, and in some implementations symmetrically, aligned with the first electrode 104. For example, when the first electrode 104 is conic in shape and an end 114 of the second electrode 106 is cylindrical, the first and second electrodes 104, 106 are positioned such that an axis extending from the conic first electrode 104 is substantially aligned with an axis extending from the cylindrical portion of the second electrode 106.

In some implementations, a distance between a tip of the first electrode 104 and a point on the second electrode 106 closest to the first electrode is 0.021 inch. However, various distances between 0.006 and 0.100 inch could be used depending on the application and the amount of energy to be transmitted.

The second electrode 106 is electrically coupled with a second electrically conductive structure 116 in the EHL probe 100. As known in the art, the second electrically conductive structure 116 may be coupled with an electrical source and used to charge the second electrode to a second polarity, which is opposite to the first polarity of the first electrode 104.

In one implementation, the first electrode 104 is an anode and the second electrode 106 is a cathode, where in other implementations, the first electrode 104 is a cathode and the second electrode 106 is an anode. When the first electrode 104 is charged to a first polarity via the first conductive structure 112 and the second electrode 106 is charged to a second, opposite polarity via the second conductive structure 114, a discharge of electricity occurs between the first and second electrodes 104, 106 (an electrical arc) when the potential between the first and second electrodes 104, 106 reaches the breakdown voltage for the media separating the electrodes.

In some implementations, such as the heart application described above, at least a portion of the lithotripsy probe tip 101 including the first and second electrodes 104, 106 is surrounded by a flexible encapsulating member 118, such as a balloon, comprising a water-tight flexible material such as Mylar. The flexible encapsulating member 118 encapsulates a liquid such as saline. However, other liquids can be used. When an electrical arc occurs between the first and second electrodes 104, 106 as described above, the electrical arc causes a steam bubble in the liquid of the flexible encapsulating member 118. The steam bubble rapidly expands and contracts back on itself. As the steam bubble contracts, a pressure wave (a shockwave) is created in the liquid of the flexible encapsulating member 118 that radiates away from the lithotripsy tip 101 in a substantially radial manner such that the shockwave is at least semi-annular. However, in other implementations, a flexible encapsulating member 118 does not surround the lithotripsy probe tip 101.

Figure 3:
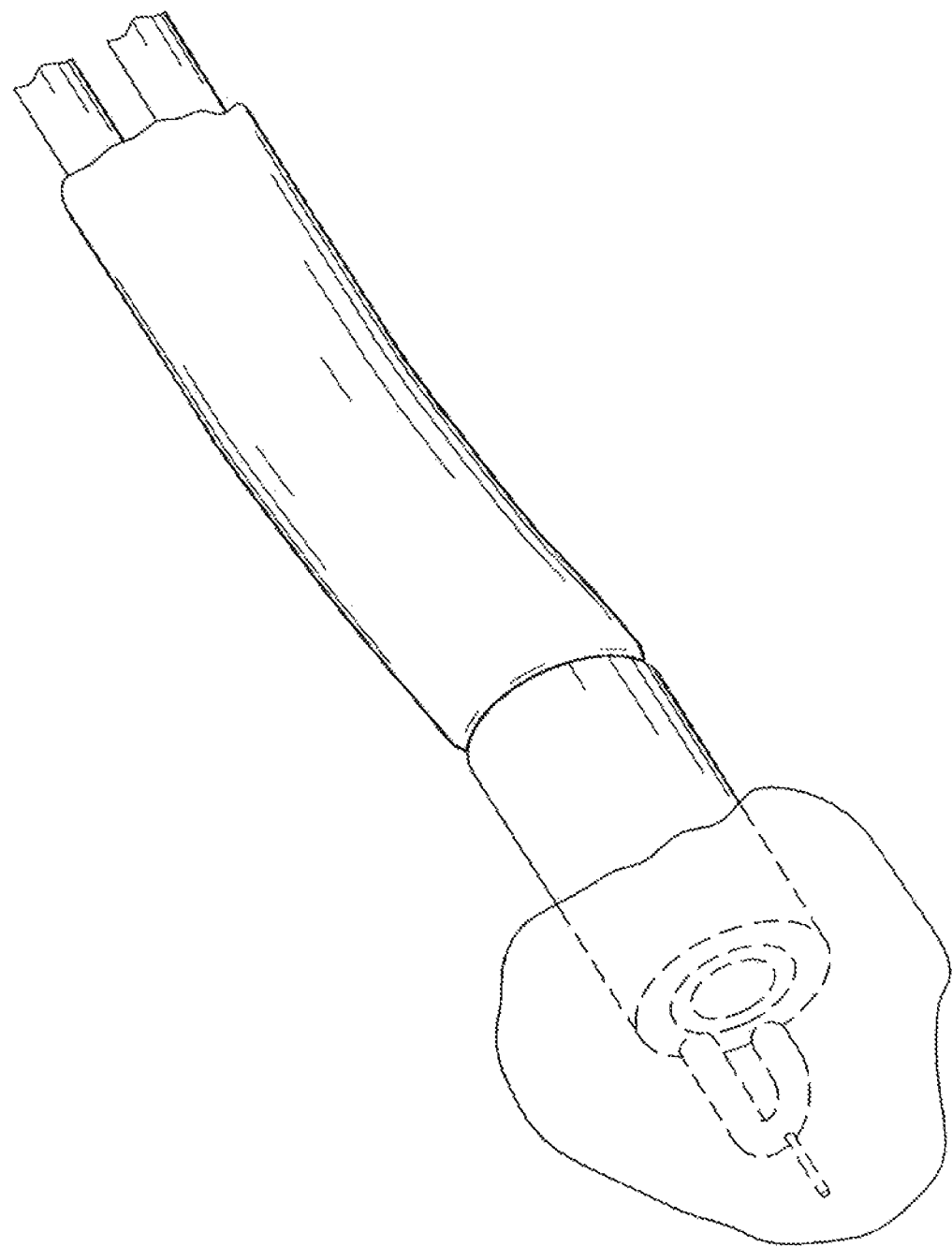
FIG. 3 is a perspective view of another embodiment of a radially-firing electrohydraulic lithotripsy probe.
Figure 4:
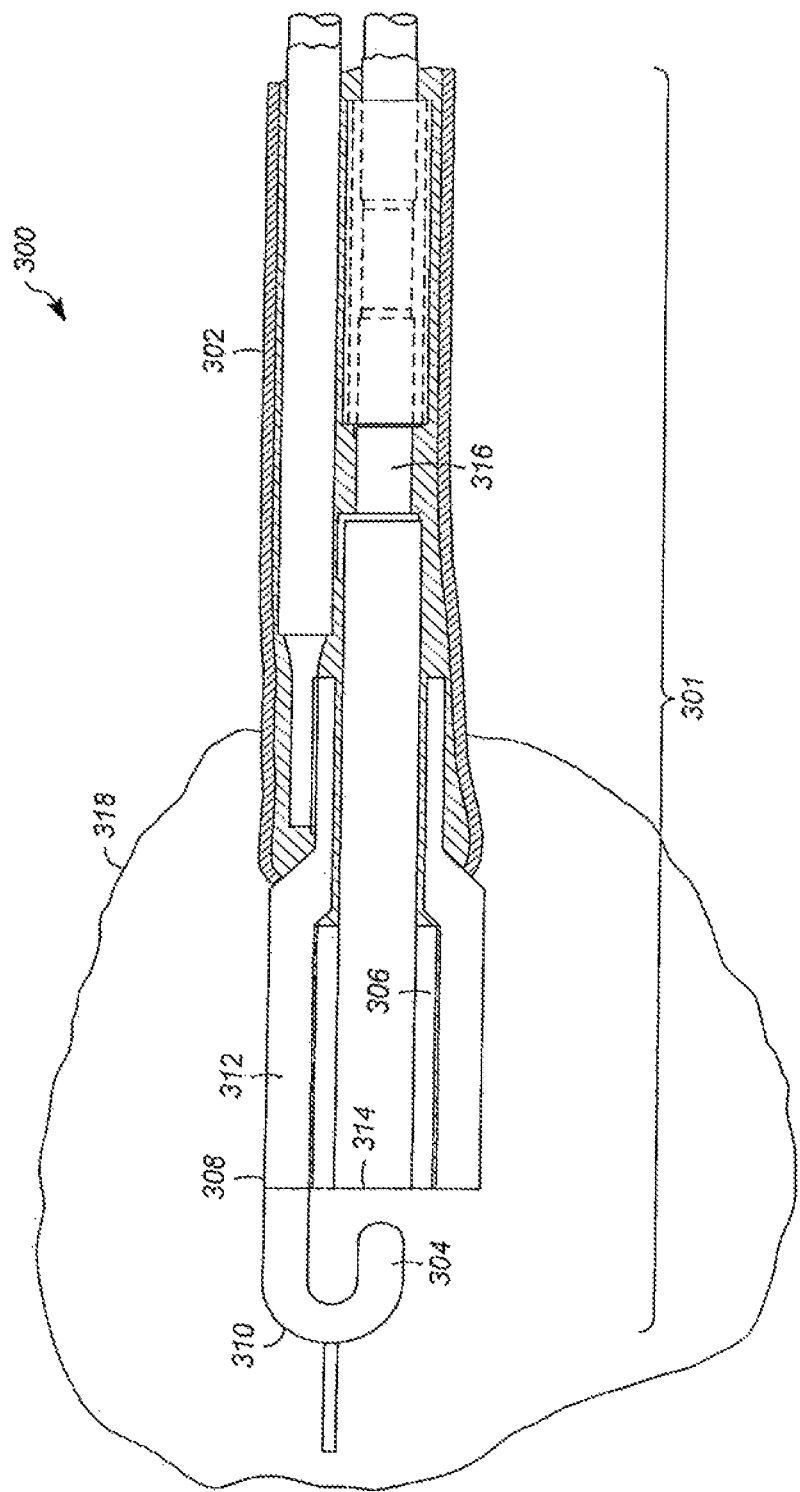
FIG. 4 is a cross-sectional side view of the radially-firing electrohydraulic lithotripsy probe of FIG. 3.

Another embodiment of a radially-firing EHL probe is described below with respect to FIGS. 3 and 4. The radially-firing EHL probe 300 (the "probe 300") includes a lithotripsy probe tip 301 including an insulating body 302, a first electrode 304, and a second electrode 306. Similar to the embodiment described above with respect to FIGS. 1 and 2, the first electrode 304 is positioned at a first distal end 308 of the lithotripsy probe tip 301. The first electrode 304 is positioned on an end of a hook structure 310 extending from the first distal end 308 of the lithotripsy probe tip 301. The hook structure 310 may be other shapes that extend from the first distal end 308 of the lithotripsy probe tip 301 and curve back towards the lithotripsy probe tip 301 so that the first electrode 304 may be positioned at an end of the structure 310 and coaxially aligned with the second electrode 306 as explained in more detail below.

The hook structure 310 includes an electrically conductive material such as copper, silver, stainless steel, or other conductive materials, and is electrically coupled with a first electrically conductive structure 312 in the EHL probe 300. In some implementations, the hook structure 310 is insulated other than where the hook structure 310 is electrically coupled with the first electrode 304 and at the first electrode 304. As known in the art, the first electrically conductive structure 312 may be electrically coupled with an electrical source and used to charge the first electrode 304 to a first polarity.

The second electrode 306 is positioned in body of the lithotripsy probe tip 301. In one implementation, at least an end 314 of the second electrode 306 is cylindrical and includes an electrically conductive material such as copper, silver, stainless steel, or other conductive materials. However, the second electrode 306 may be other shapes. The second electrode 306 is positioned in the lithotripsy probe tip 301 such that the second electrode 306 is coaxially, and in some implementations symmetrically, aligned with the first electrode 304. For example, when an end 314 of the second electrode 306 is cylindrical, an axis extending from the cylindrical portion of the second electrode 306 is substantially aligned with the first electrode 304 positioned on the hook structure 310.

In some implementations, a distance between the first electrode 304 and a point on the second electrode 306 closest to the first electrode is 0.021 inch. However, various distances between 0.006 and 0.100 inch could be used depending on the application and the amount of energy to be transmitted.

The second electrode 306 is electrically coupled with a second electrically conductive structure 316 in the EHL probe 300. As known in the art, the second electrically conductive structure 316 may be electrically coupled with an electrical source and used to charge the second electrode to a second polarity, which is opposite to the first polarity of the first electrode 304.

In one implementation, the first electrode 304 is an anode and the second electrode 306 is a cathode, where in other implementations, the first electrode 304 is a cathode and the second electrode 306 is an anode. When the first electrode 304 is charged to a first polarity via the first electrically conductive structure 312 and the second electrode 306 is charged to a second, opposite polarity via the second electrically conductive structure 314, a discharge of electricity occurs between the first and second electrodes 304, 306 (an electrical arc) when the potential between the first and second electrodes 304, 306 reaches the breakdown voltage for the media separating the electrodes.

In some implementations, at least a portion of the lithotripsy probe tip 301 including the first and second electrodes 304, 306 is surrounded by a flexible encapsulating member 318, such as a balloon, comprising a water-tight flexible material such as Mylar. The flexible encapsulating member 318 encapsulates a liquid such as saline. However, other liquids can be used. When an electrical arc occurs between the first and second electrodes 304, 306 as described above, the electrical arc causes a steam bubble in the liquid of the flexible encapsulating member 318. The steam bubble rapidly expands and contracts back on itself. As the steam bubble contracts, a pressure wave (a shockwave) is created in the liquid of the flexible encapsulating member 118 that radiates away from the lithotripsy tip 301 in a radial manner such that the shockwave is at least semi-annular. However, in other implementations, a flexible encapsulating member 318 does not surround the lithotripsy probe tip 301.

Figure 5:
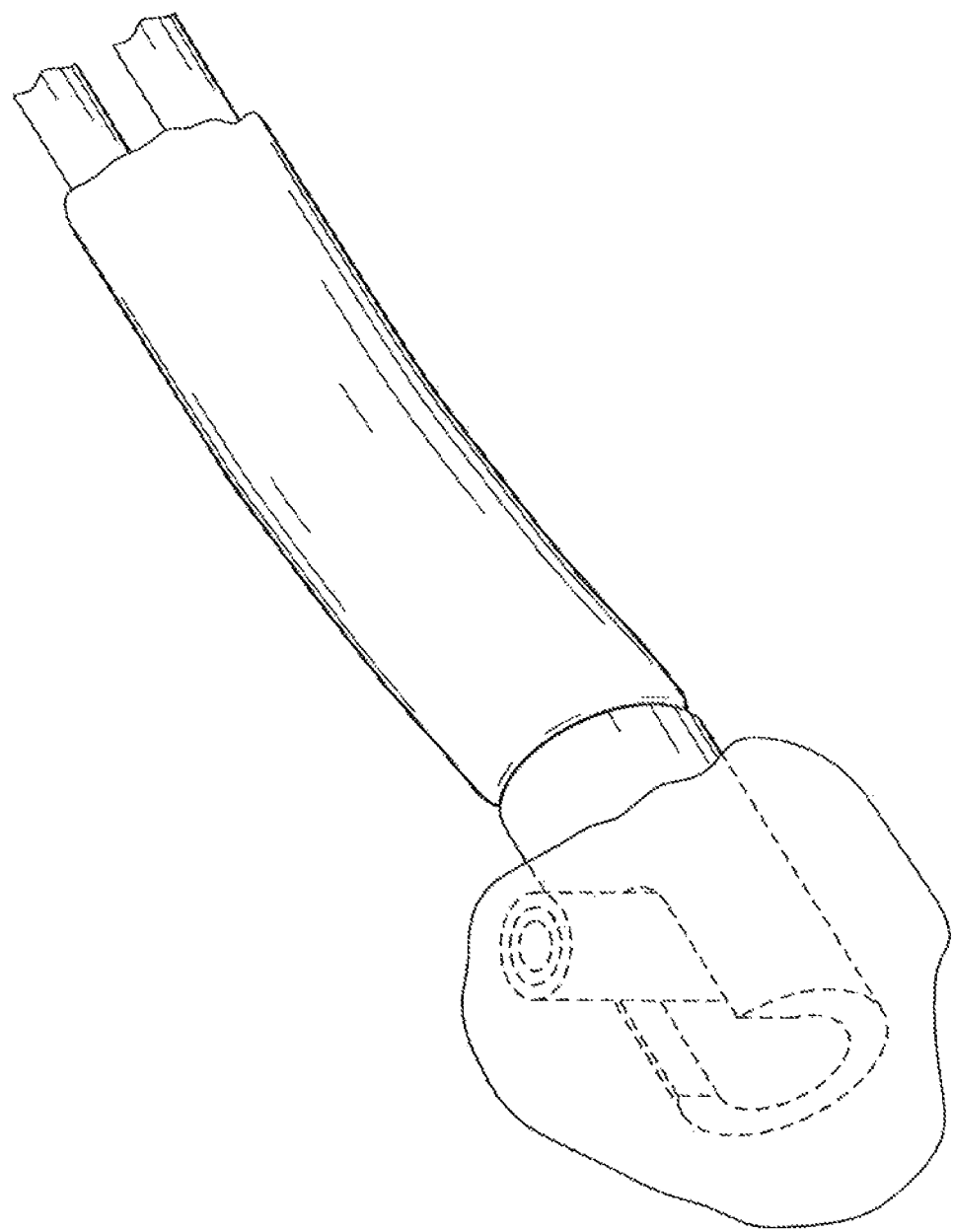
FIG. 5 is a perspective view of another embodiment of a radially-firing electrohydraulic lithotripsy probe.
Figure 6:
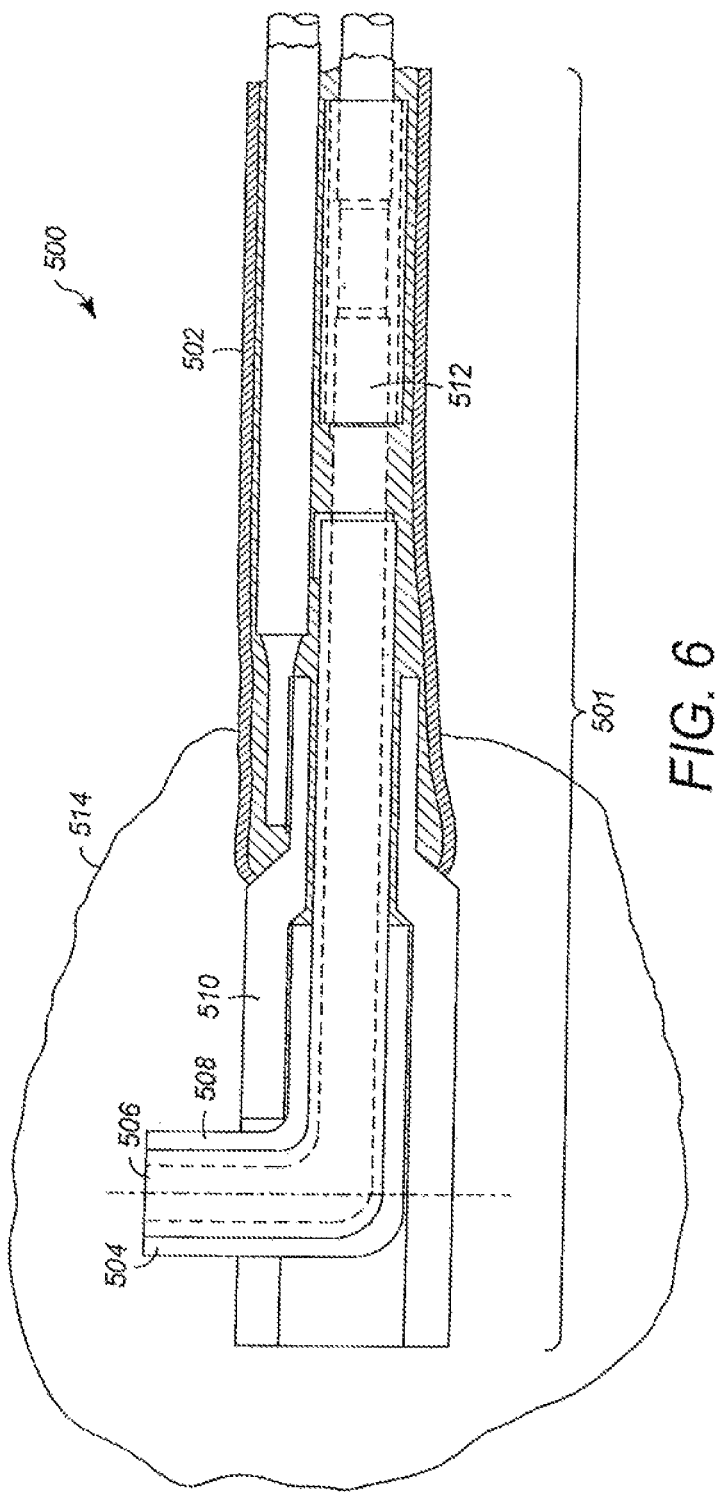
FIG. 6 is a cross-sectional side view of the radially-firing electrohydraulic lithotripsy probe of FIG. 5.
Figure 7:
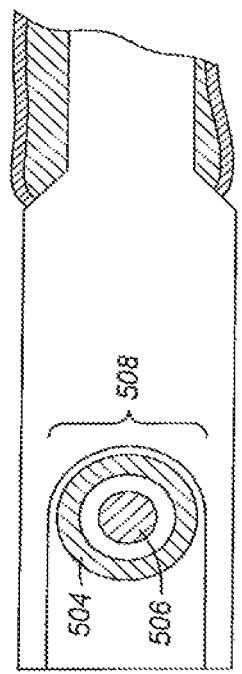
FIG. 7 is a side view of the radially-firing electrohydraulic lithotripsy probe of FIG. 5.

Yet another embodiment of a radially-firing EHL probe is described below with respect to FIGS. 5, 6, and 7. The radially-firing EHL probe 500 (the "probe 500") includes a lithotripsy probe tip 501 including an insulating body 502, a first electrode 504, and a second electrode 506. The first and second electrodes 504, 506 are positioned on a side-firing structure 508 of the lithotripsy probe tip 501. An axis of the side-firing structure 508 is typically angled approximately 90 degrees from the longitudinal axis of the lithotripsy probe 501 so that, as explained below, the lithotripsy probe tip 501 may create a directed shockwave that radiates away from the lithotripsy probe tip 501 at approximately a 90 degree angle from the longitudinal axis of the lithotripsy probe 501.

In one implementation, the first electrode 504 may be a cylindrical sleeve positioned on an exterior of the side-firing structure 508. However, the first electrode 504 may be other shapes. The first electrode 504 is electrically coupled with a first electrically conductive structure 510 in the EHL probe 500. As known in the art, the first electrically conductive structure 510 may be electrically coupled with an electrical source and used to charge the first electrode 504 to a first polarity.

The second electrode 506 is coaxially aligned with the first electrode 504. In one implementation, the first electrode 504 is a cylindrical sleeve and the second electrode 506 is a cylindrical core that is positioned within the interior of the first electrode 504 such that the axis of the cylindrical sleeve of the first electrode 504 substantially aligns with the cylindrical core of the second electrode 506.

The second electrode 506 is electrically coupled with a second electrically conductive structure 512 in the EHL probe 500. As known in the art, the second electrically conductive structure 512 may be electrically coupled with an electrical source and used to charge the second electrode 506 to a second polarity, which is opposite to the first polarity of the first electrode 504.

In one implementation, the first electrode 504 is an anode and the second electrode 506 is a cathode, where in other implementations, the first electrode 504 is a cathode and the second electrode 506 is an anode. When the first electrode 504 is charged to a first polarity via the first conductive structure 510 and the second electrode 506 is charged to a second, opposite polarity via the second conductive structure 512, a discharge of electricity occurs between the first and second electrodes 504, 506 (an electrical arc) when the potential between the first and second electrodes 504, 506 reaches the breakdown voltage for the media separating the electrodes.

In some implementations, at least a portion of the lithotripsy probe tip 501 including the first and second electrodes 504, 506 is surrounded by a flexible encapsulating member 514, such as a balloon, comprising a water-tight flexible material such as Mylar. The flexible encapsulating member 514 encapsulates a liquid such as saline. However, other liquids can be used. When an electrical arc occurs between the first and second electrodes 504, 506 as described above, the electrical arc causes a steam bubble in the liquid of the flexible encapsulating member 514. The steam bubble rapidly expands and contracts back on itself. As the steam bubble contracts, a pressure wave (a shockwave) is created in the liquid of the flexible encapsulating member 514 that radiates away from the side-firing structure 508 in an axial manner, so that the shockwave radiates away from the lithotripsy probe tip 501 in a radial manner. However, in other implementations, a flexible encapsulating member 514 does not surround the lithotripsy probe tip 501.

One concern with EHL probes is a breakdown of the EHL probe, also known as the End of Life of an EHL probe. In some implementations, an electrical source such as an electrohydraulic generator connected to an EHL probe may track a number of times it fires an EHL probe. Based on the number of times the EHL probe fires, power levels used during the firing of the EHL probe, and historical End of Life data for EHL probes, the electrical source may then determine when the EHL probe is nearing End of Life.

When an EHL probe nears End of Life, an electrical source may display messages such as "End of Life" or "Change Probe" to warn a doctor to dispose of an EHL probe. In some implementations, an EHL probe may be designed to disable the EHL probe after reaching or nearing End of Life.

Figure 8A:
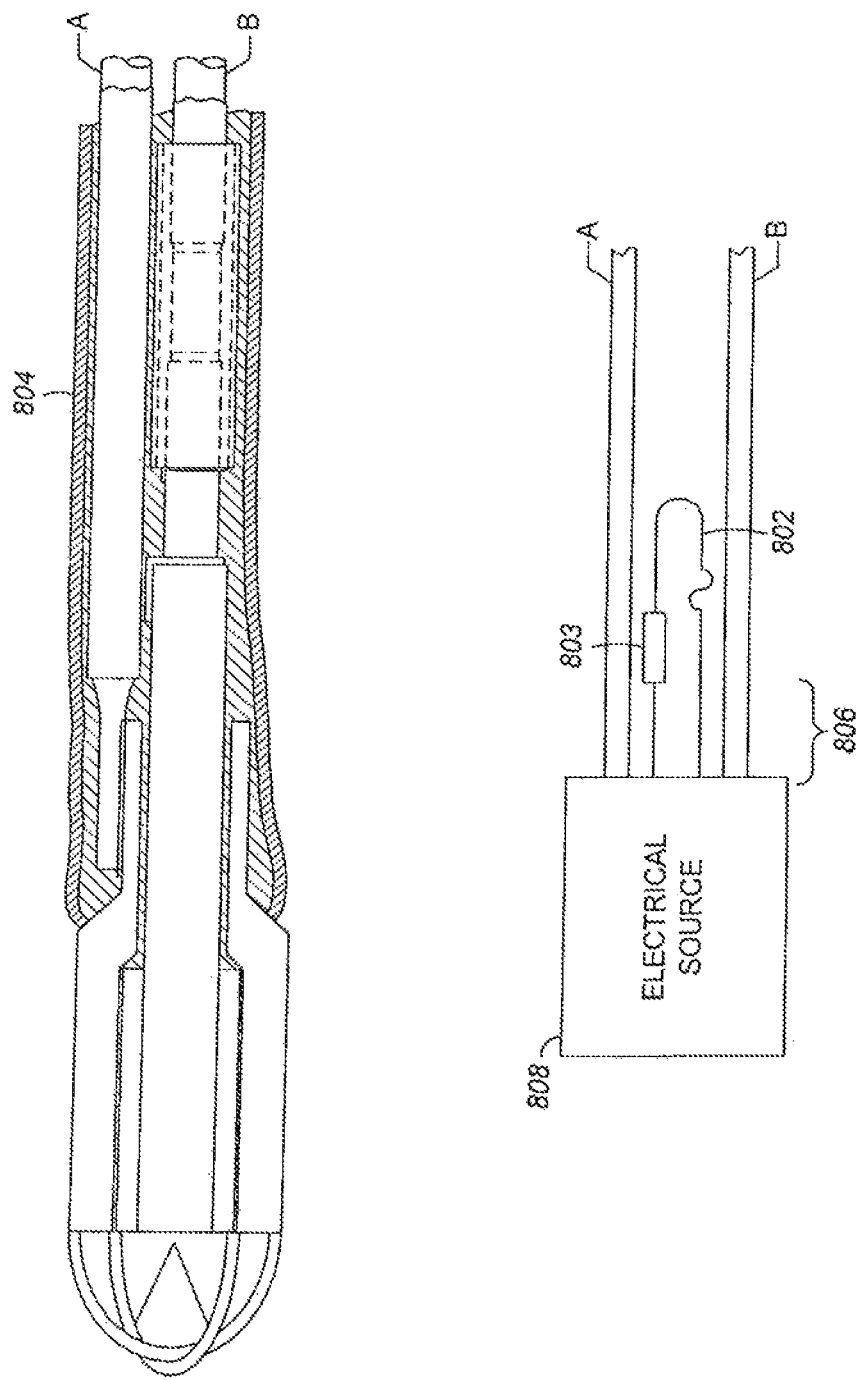
FIG. 8*a* is a cross-section of an EHL probe including a fusible link.

FIG. 8a is a cross-section of an EHL probe 804 including a fusible link 802. Generally, the fusible link 802 is used to disable the EHL probe 804 when the EHL probe nears End of Life. In one implementation, the fusible link 802 may be placed in a connector 806 of the EHL probe 804. However, in other implementations, the fusible link 802 may be placed in other portions of the EHL probe 804.

Generally, an electrical source 808 monitors a number of times the EHL probe 804 fires and power levels used during firing of the EHL probe 804. The electrical source 808 compares the number of times the EHL probe 804 fires and power levels used during firing of the EHL probe 804 to historical End of Life data for EHL probes. When the electrical source 808 determines the EHL probe 804 is near End of Life, the electrical source 808 send a short blast of high current to the EHL probe 804. In one implementation, the short blast of high current is 150 milliamps. When the short blast of high current reaches the fusible link 802 in the EHL probe 804, the high current causes a fuse within the fusible link 802 to "open" (vaporizing some of the wire to open a circuit), thereby disabling the EHL probe 804. In some implementations, the fusible link 802 includes a sense resistor 803 placed between two pins, however other implementations do not include the sense resistor 803.

In some implementations, the electrical source 808 may measure an interior resistance of an EHL probe 804 so that the electrical source 808 can determine when the EHL probe 804 has been disabled.

Figure 8B:
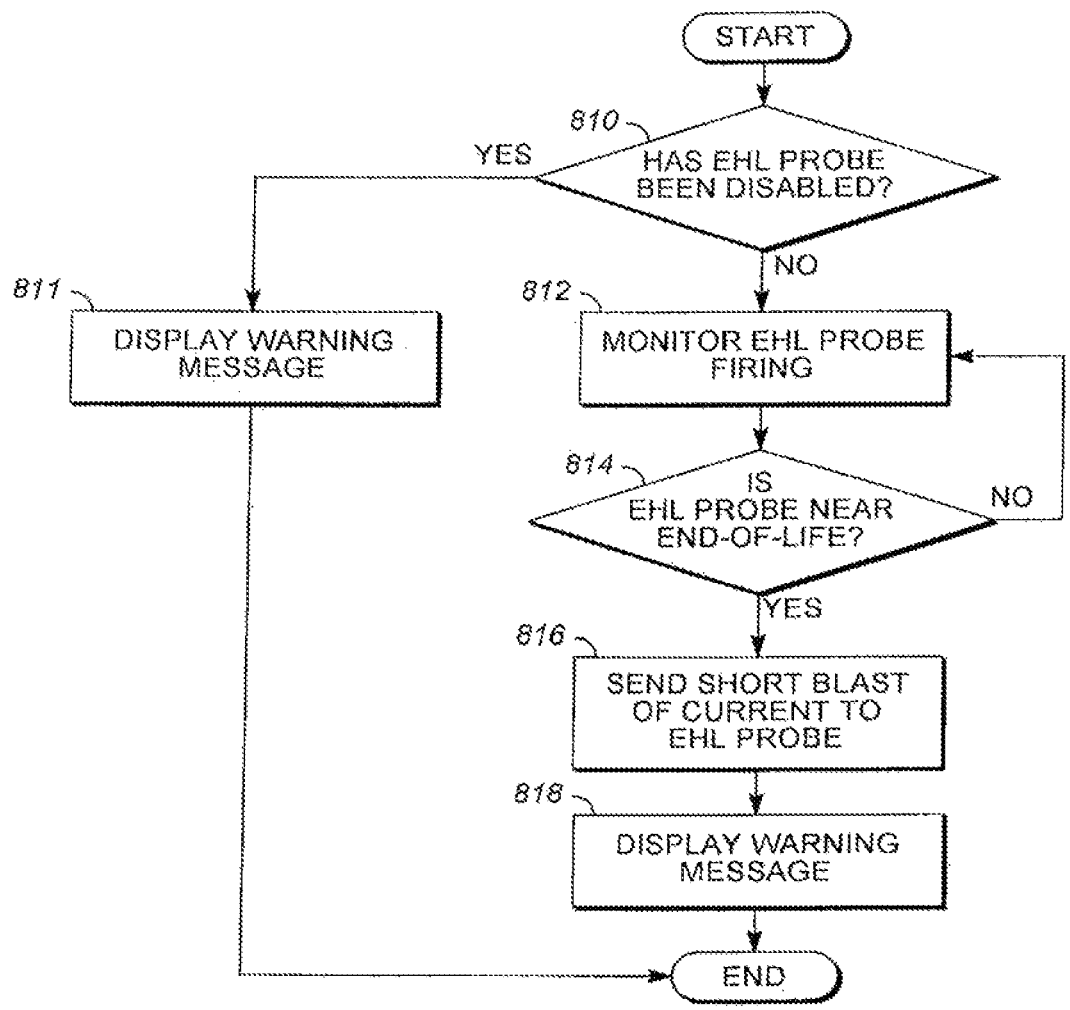
FIG. 8*b* is a flow chart for a method of using the EHL probe of FIG. 8*a*.

FIG. 8b is a flow chart of a method for using the EHL probe described above with respect to FIG. 8a. At step 810 an electrical source measures an interior resistance of an EHL probe to determine whether the EHL probe has been disabled. The electrical source may perform step 810 when the EHL probe is first connected to the electrical source, periodically, before each firing of the EHL probe, and/or after each firing of the EHL probe.

If the electrical source determines at step 810 that the EHL probe has been disabled, the method proceeds to step 811 where the electrical source displays a message such as "End of Life" or "Change Probe" to warn a doctor to dispose of the EHL probe. However, if the electrical source determines at step 810 that the EHL probe has not been disabled, the method proceeds to step 812 where the electrical source monitors a number of times an EHL probe fires and power levels used during firing of the EHL probe.

At step 814, the electrical source compares the number of times the EHL probe has fired and the power levels used during firing of the EHL probe to historical End of Life data for EHL probes to determine whether the EHL probe is near End of Life. The electrical source may perform step 814 periodically, before each firing of the EHL probe, and/or after each firing of the EHL probe.

If the electrical source determines at step 814 that the EHL probe is not near End of Life, the method loops to step 812 and the electrical source continues to monitor the number of times an EHL probe fires and power levels used during firing of the EHL probe. However, if the electrical source determines at step 812 that the EHL probe is near End of Life, the method proceeds to step 816.

At step 816, the electrical source sends a short blast of high current to the EHL probe to cause a fuse within the fusable link of the EHL probe to open, thereby disabling the EHL probe. At step 818, the electrical source may display a message such as "End of Life" or "Change Probe" to warn a doctor to dispose of the EHL probe.

It will be appreciated that the order of the one or more steps of the method described with respect to FIG. 8*b* may be changed. Further, in some implementations, the method of FIG. 8*b* may be implemented in conjunction with a computer-readable storage medium comprising a set of instructions to direct a processor of the electrical source to perform one or more of the above-described acts.

Figure 9A:
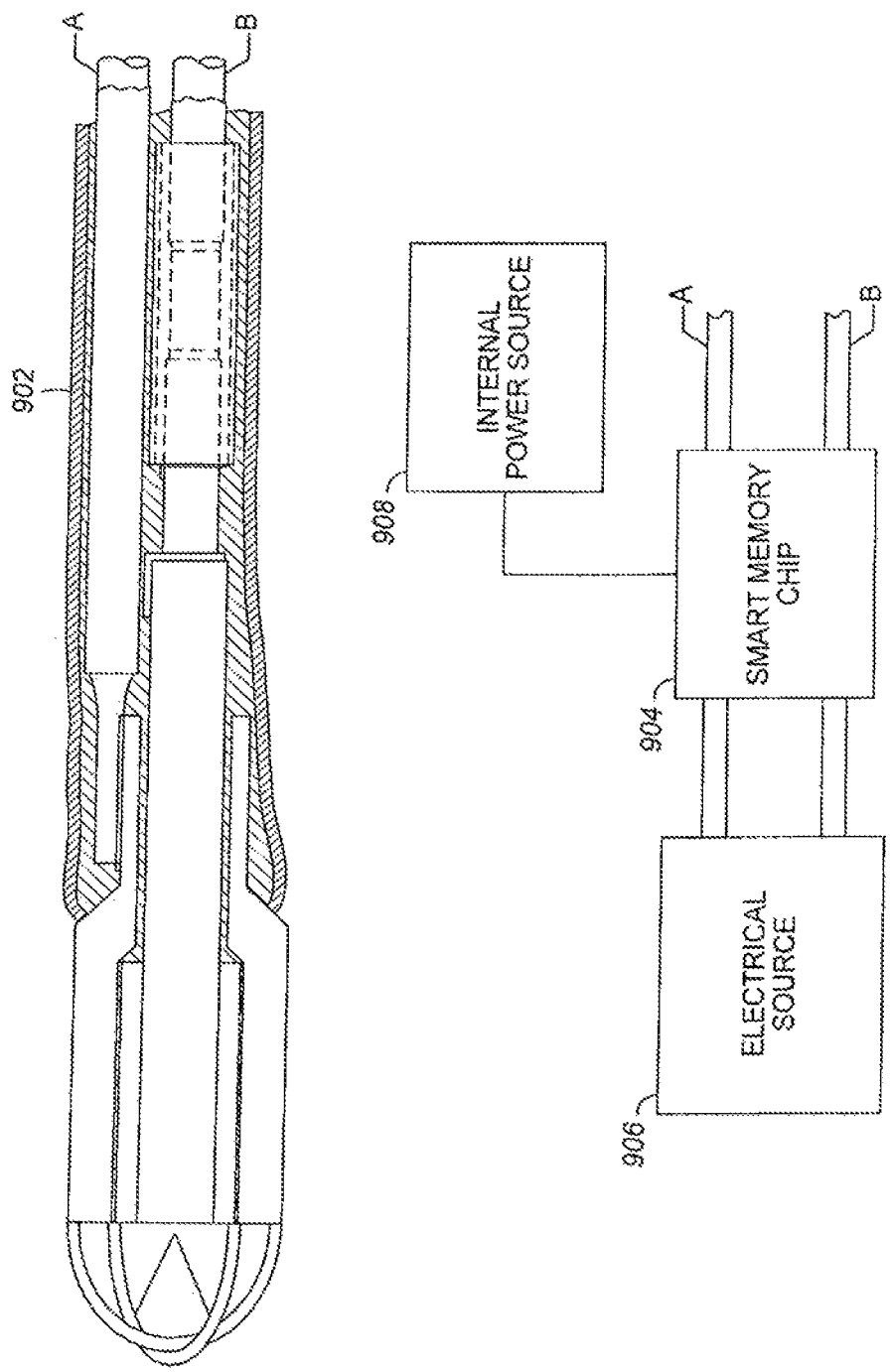
FIG. 9*a* is a cross-section of an EHL probe including a smart memory chip.

FIG. 9*a* is a cross-section of an EHL probe 902 including a smart memory chip 904. The smart memory chip 904 may be any flash memory device small enough to be positioned in a connector of the EHL probe 902. One example of such a flash memory device is a 128 k×8 monolithic flash chip by White Electronics Designs Corp. (part number WMF-128 k8-xclx5). Generally, each time an electrical source 906 fires the EHL probe 902, the electrical source 906 also sends a count signal to the smart memory chip 904. The smart memory chip 904 monitors a number of times the EHL probe 902 has been fired. When the EHL probe 902 is near End of Life, the smart memory chip 904 may disable the EHL probe 902 and prevent the EHL probe 902 from firing.

In some implementations, the EHL probe 902 may include an internal power source 908 such as a battery so that the smart memory chip 904 may maintain a count of the number of times the EHL probe 902 has fired even when the EHL probe 902 is disconnected from the electrical source 906. In some implementations the smart memory chip 904 may additionally include a unique identifier, such as a serial number, so that the EHL probe 902 is uniquely identified to the electrical source 906 when the EHL probe 902 is first connected to the electrical source 906. The electrical source 906 may use the unique identifier for purposes such as record keeping, performance analysis, or trouble shooting of faulty EHL probes 902.

Figure 9B:
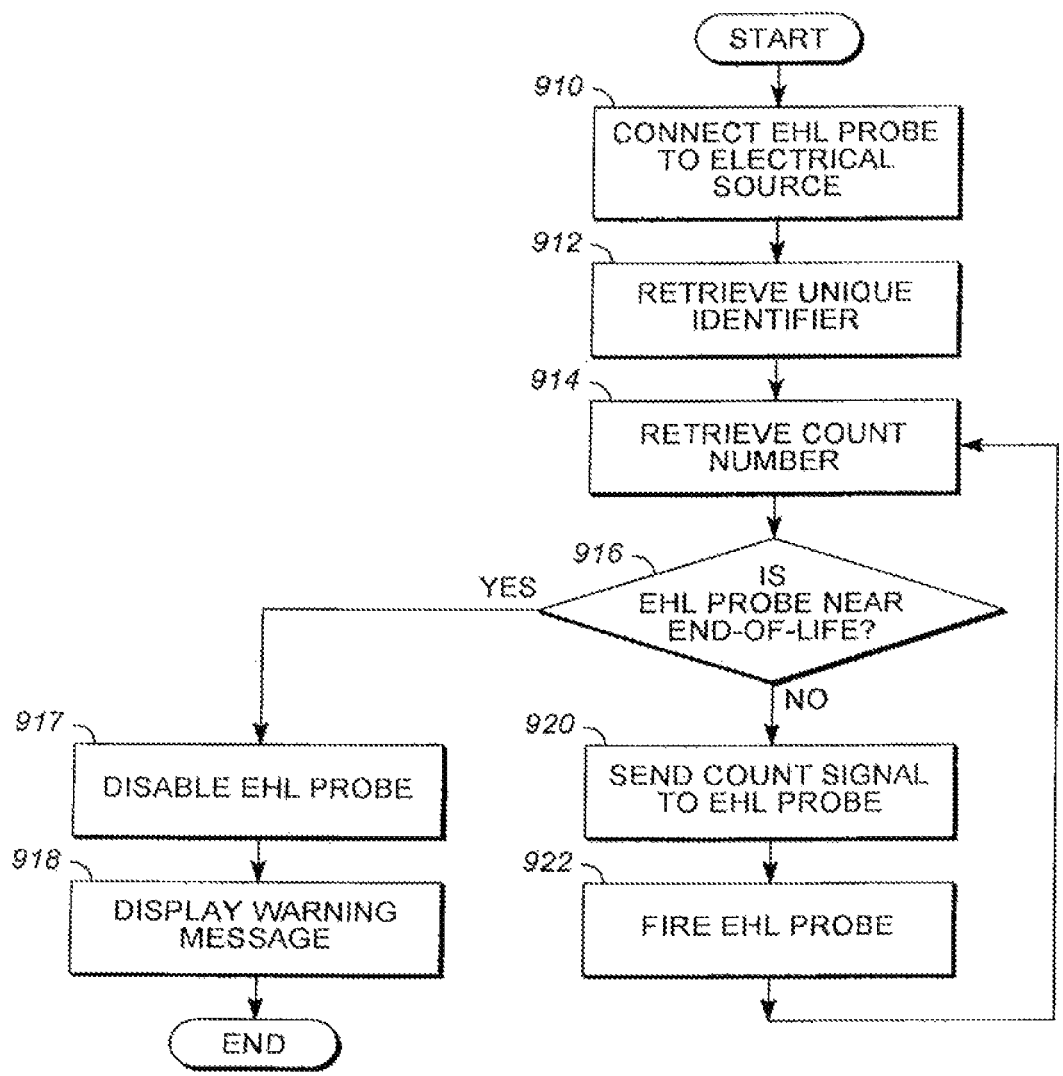
FIG. 9*b* is a flow chart of a method for using the EHL probe of FIG. 9*b*.

FIG. 9*b* is a flow chart of a method for using the EHL probe described above with respect to FIG. 9*a*. At step 910, an EHL probe is connected to the electrical source. At step 912, the electrical source retrieves a unique identifier from a memory of the EHL probe to identify the EHL probe to the electrical source.

At step 914, the electrical source retrieves a count of a number of times the EHL probe has been fired from the memory of the EHL probe. At step 916, the electrical source determines whether the EHL probe is near End of Life by comparing the number of times the EHL probe has been fired to a threshold.

If the electrical source determines at step 916 that the EHL probe is near End of Life, the electrical source disables the EHL probe at step 917. Additionally, the electrical source may display a message such as "End of Life" or "Change Probe" to warn a doctor to dispose of the EHL probe at step 918.

However, if the electrical source determines at step 916 that the EHL probe is not near End of Life, the method proceeds to step 920 where the electrical source sends a count signal to the memory of the EHL probe to increment the number of times the EHL probe has been fired. At step 922, the electrical source fires the EHL probe. The method then loops to step 914.

It will be appreciated that the order of one or more steps of the method described above with respect to FIG. 9*b* may be changed. For example, the electrical source may fire the EHL probe (step 922) before incrementing the number of times the EHL probe has been fired (step 920). Further, in some implementations, the method of FIG. 9*b* may be implemented in conjunction with a computer-readable storage medium comprising a set of instructions to direct a processor of the electrical source to perform one or more of the above-described acts.

Figure 10A:
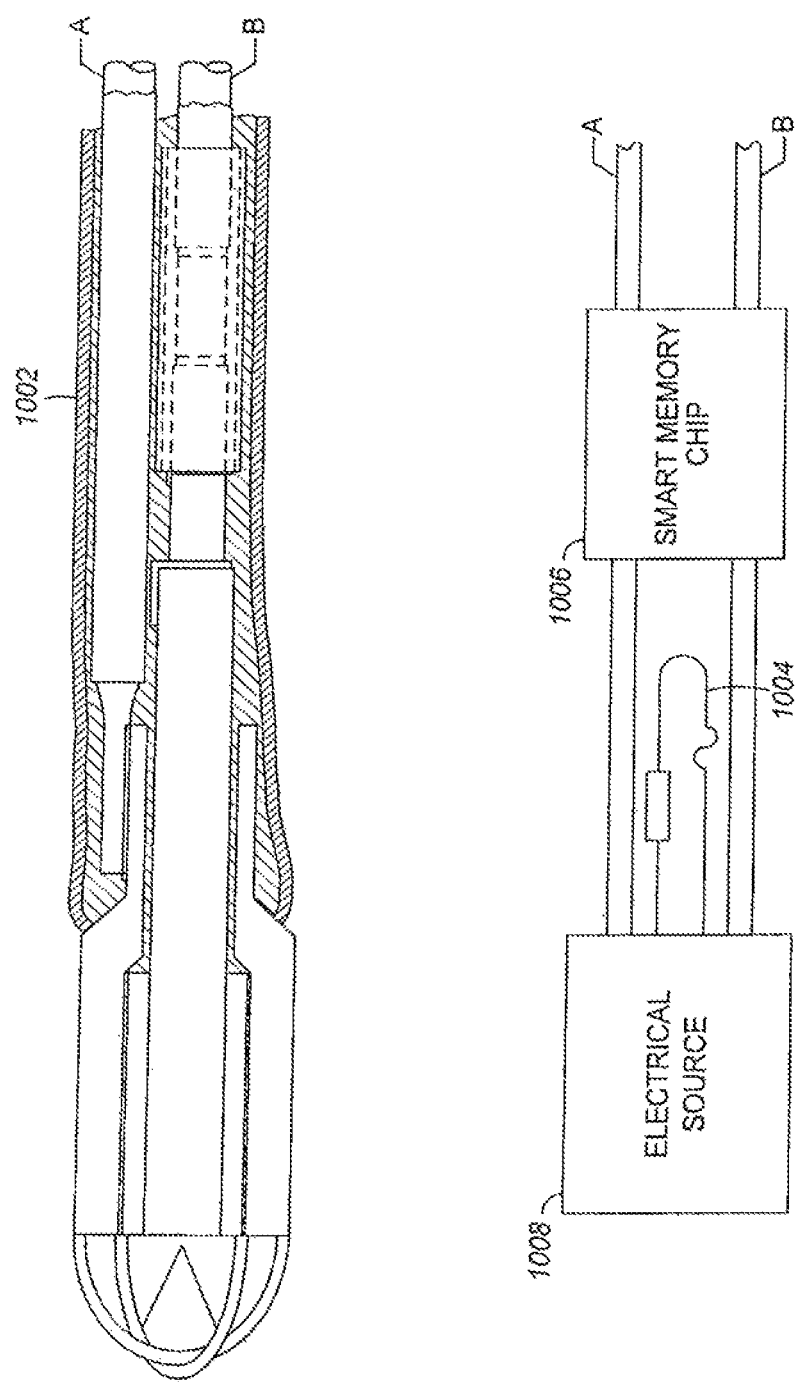
FIG. 10*a* is a cross-section of an EHL probe including a fusible link and a smart memory chip.

FIG. 10*a* is a cross-section of an EHL probe 1002 including a fusible link 1004 and a smart memory chip 1006. It will be appreciated that in implementations including both the fusible link 1004 and the smart memory chip 1006, the fusible link 1004 may function as described above in conjunction with FIG. 8 to disable the EHL probe 1002 in response to a short blast of high current from an electrical source 1008. Additionally, the smart memory chip 1006 may function as described above in conjunction with FIG. 9 to disable the EHL probe 1002 when the smart memory chip 1006 determines based on a number of times the EHL probe 1002 has fired that the EHL probe 1002 is near End of Life.

Figure 10B:
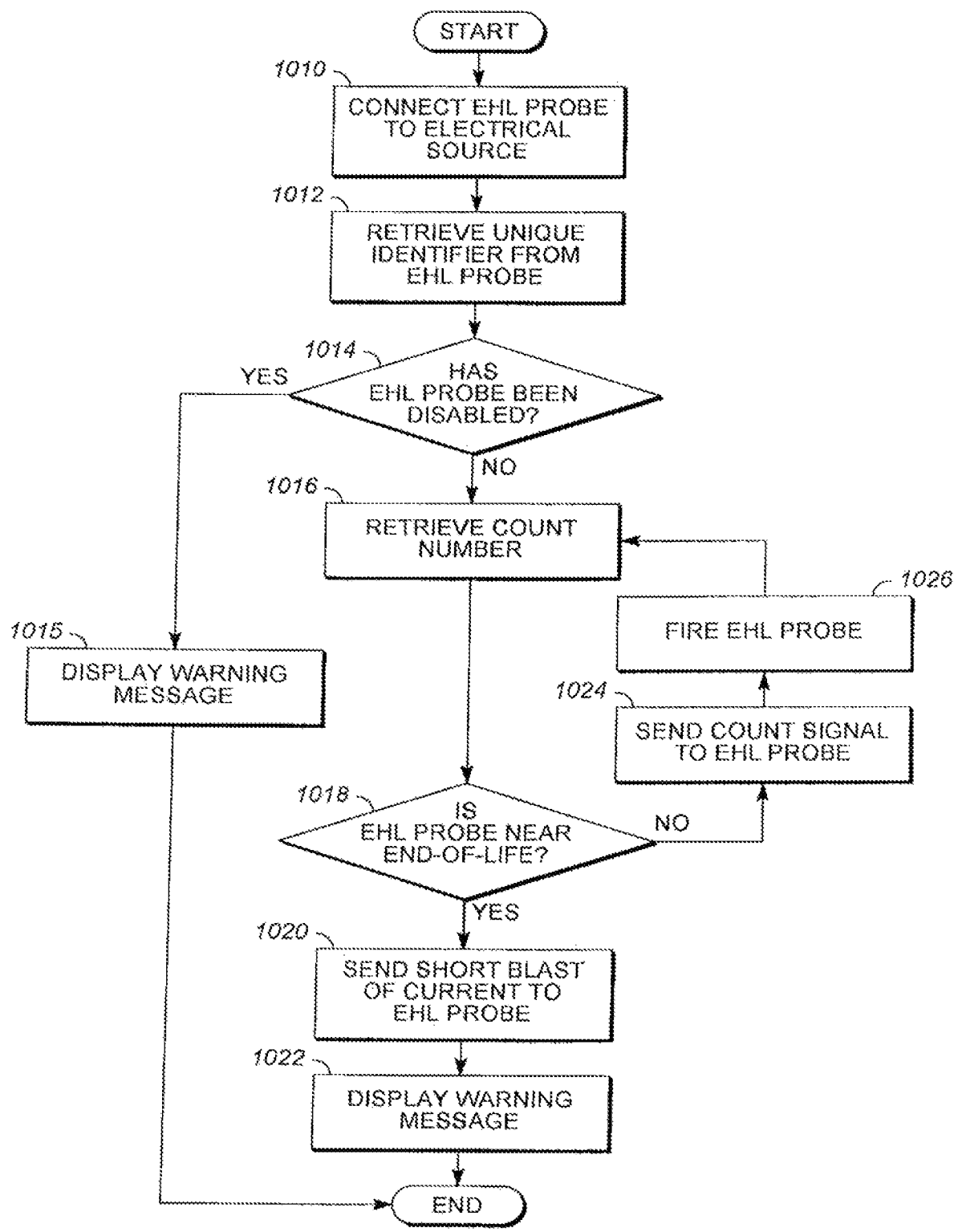
FIG. 10*b* is a flow chart of a method for using the EHL probe of FIG. 10*b*.

FIG. 10*b* is a flow chart of a method for using the EHL probe of FIG. 10*a*. At step 1010, an EHL probe is connected to the electrical source. At step 1012, the electrical source retrieves a unique identifier from a memory of the EHL probe to identify the EHL probe to the electrical source. At step 1014, the electrical source measures an interior resistance of the EHL probe to determine whether the EHL probe has been disabled.

If the electrical source determines at step 1014 that the EHL probe has been disabled, the method proceeds to step 1015 where the electrical source displays a message such as "End of Life" or "Change Probe" to warn a doctor to dispose of the EHL probe. However, if the electrical source determines at step 1014 that the EHL probe has not been disabled, the method proceeds to step 1016.

At step 1016, the electrical source retrieves a count of a number of times the EHL probe has been fired from the memory of the EHL probe. At step 1018, the electrical source determines whether the EHL probe is near End of Life by comparing the number of times the EHL probe has been fired to a threshold.

If the electrical source determines at step 1018 that the EHL probe is near End of Life, the method proceeds to step 1020 where the electrical source sends a short blast of high current to the EHL probe to cause a fuse within the fusable link of the EHL probe to open, thereby disabling the EHL probe. At step 1022, the electrical source may display a message such as "End of Life" or "Change Probe" to warn a doctor to dispose of the EHL probe.

If the electrical source determines at step 1018 that the EHL probe is not near End of Life, the method proceeds to step 1024 where the electrical source sends a count signal to the memory of the EHL probe to increment the number of times the EHL probe has been fired. At step 1026, the electrical source fires the EHL probe. The method then loops to step 1016.

It will be appreciated that the order of one or more steps of the method described above with respect to FIG. 10*b* may be changed. Further, in some implementations, the method of FIG. 10*b* may be implemented in conjunction with a computer-readable storage medium comprising a set of instructions to direct a processor of the electrical source to perform one or more of the above-described acts.

Figure 11A:
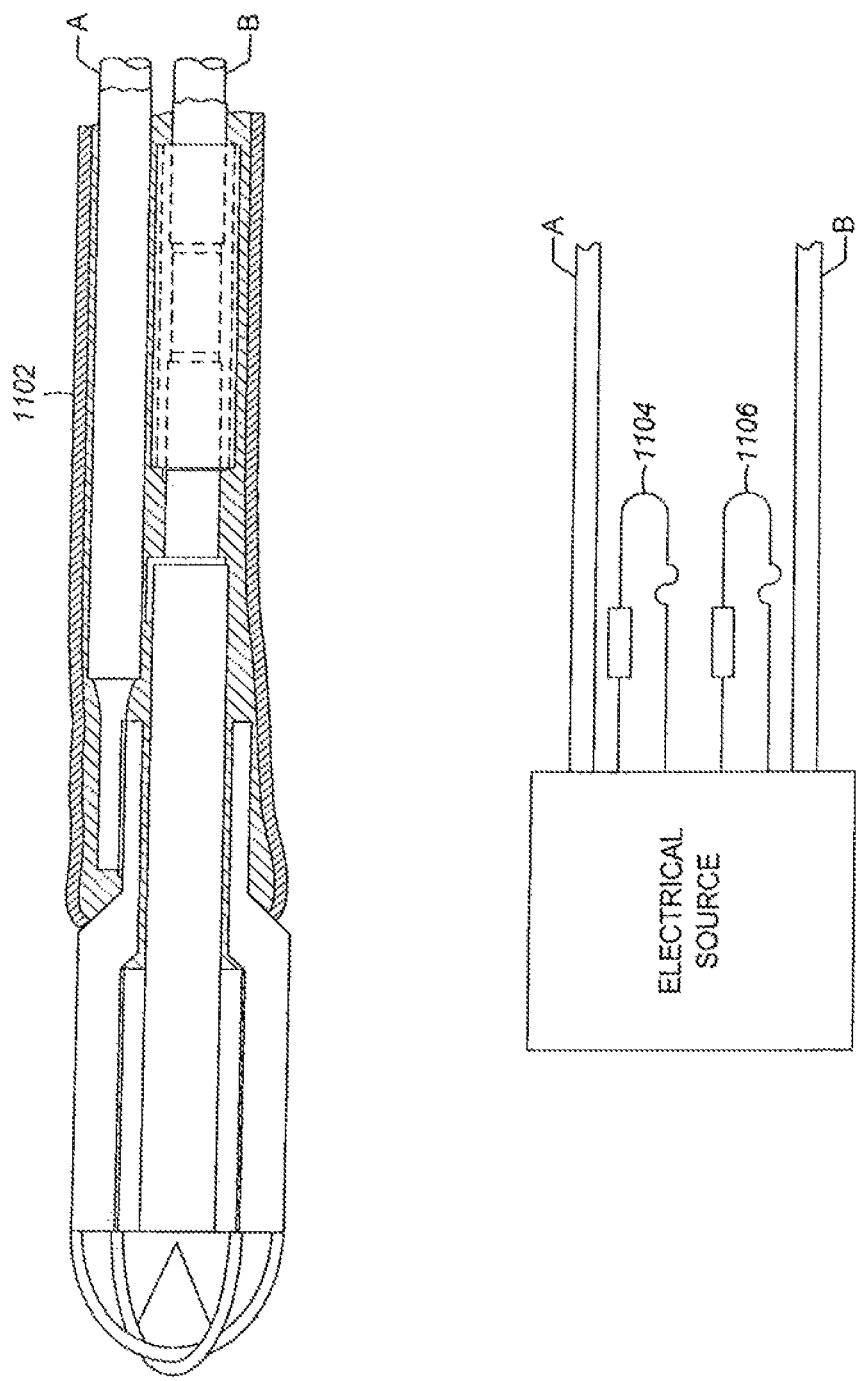
FIG. 11*a* is a cross-section of an EHL probe including a first fusible link and a second fusible link.

FIG. 11*a* is a cross-section of an EHL probe 1102 including a first fusible link 1104 and a second fusible link 1106. Generally, when the EHL probe 1102 is first fired, the first fusible link 1104 is blown so that the EHL probe cannot be reused (protecting its single use designation). Additionally, when an electrical source determines the EHL probe 1102 is near End of Life, the electrical source may send a short blast of high current to the EHL probe 1102 to blow the second fusible link 1106 as described above in conjunction with FIG. 8, thereby disabling the EHL probe 1102.

Figure 11B:
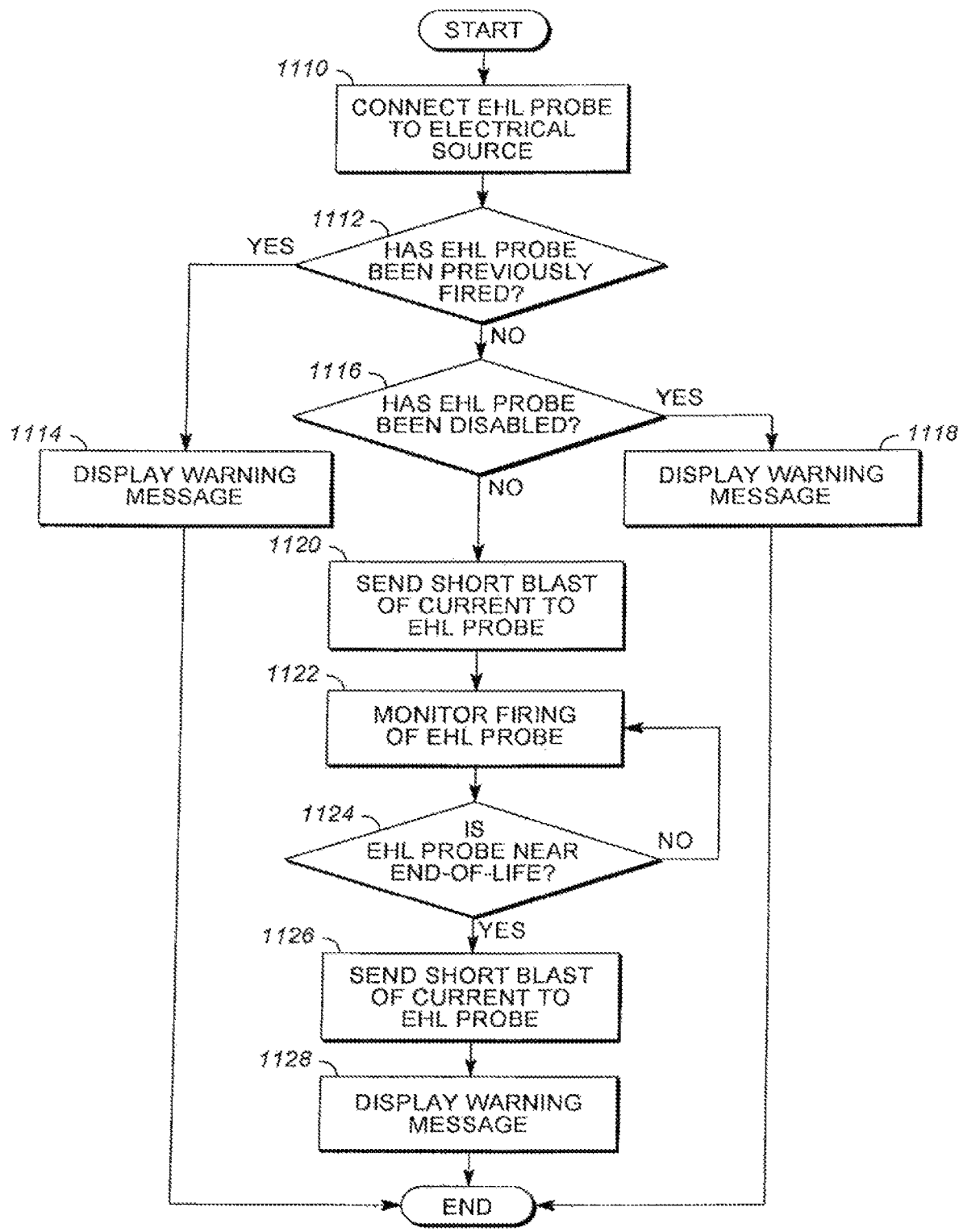
FIG. 11*b* is a flow chart of a method for using the EHL probe of FIG. 11*a*.

FIG. 11*b* is a flow chart of a method for using the EHL probe described above with respect to FIG. 11*a*. At step 1110 an EHL probe is connected to an electrical source. At step 1112, the electrical source measures an interior resistance of the EHL probe with respect to a first fuse to determine if the EHL probe has been previously fired. If the electrical source determines at step 1112 that the EHL probe has been fired, the method proceeds to step 1114 where the electrical source displays a message such as "End of Life" or "Change Probe" to warn a doctor to dispose of the EHL probe.

If the electrical source determines at step 1112 that the EHL probe has not been previously fired, the method proceeds to step 1116 where the electrical source measures an interior resistance of the EHL probe with respect to a second fuse to determine whether the EHL has been disabled because it is near End of Life. If the electrical source determines at step 1116 that the EHL probe has been disabled, the method proceeds to step 1118 where the electrical source displays a message such as "End of Life" or "Change Probe" to warn a doctor to dispose of the EHL probe.

If the electrical source determines at step 1118 that the EHL probe has not been disabled, the method proceeds to step 1120 where the electrical source sends a short blast of high current to the EHL probe to cause the first fuse within the fuseable link of the EHL probe to open before the EHL probe is fired for the first time. At step 1122 the electrical source monitors a number of times an EHL probe fires and power levels used during firing of the EHL probe.

At step 1124, the electrical source compares the number of times the EHL probe has fired and the power levels used during firing of the EHL probe to historical End of Life data for EHL probes to determine whether the EHL probe is near End of Life. If the electrical source determines at step 1124 that the EHL probe is not near End of Life, the method loops to step 1122 and the electrical source continues to monitor the number of times an EHL probe fires and power levels used during firing of the EHL probe.

If the electrical source determines at step 1124 that the EHL probe is near End of Life, the method proceeds to step 1126 where the electrical source sends a short blast of high current to the EHL probe to cause the second fuse within the fusable link of the EHL probe to open, thereby disabling the EHL probe. At step 1128, the electrical source may display a message such as "End of Life" or "Change Probe" to warn a doctor to dispose of the EHL probe.

It will be appreciated that the order one or more steps of the method described with respect to FIG. 11*b* may be changed. Further, in some implementations, the method of FIG. 11*b* may be implemented in conjunction with a computer-readable storage medium comprising a set of instructions to direct a processor of the electrical source to perform one or more of the above-described acts.

Because of the delicate nature of small EHL probes and the long paths that may be required to insert an EHL probe through body channels or through sheaths or endoscopes, EHL probes in excess of 250 cm are desirable. The EHL probes described above with respect to FIGS. 1-11 may be constructed to allow for insertion of the EHL probe into channel in excess of 250 cm by improving a linear strength of the EHL probe without significantly reducing the performance or flexibility of the EHL probe.

Figure 12:
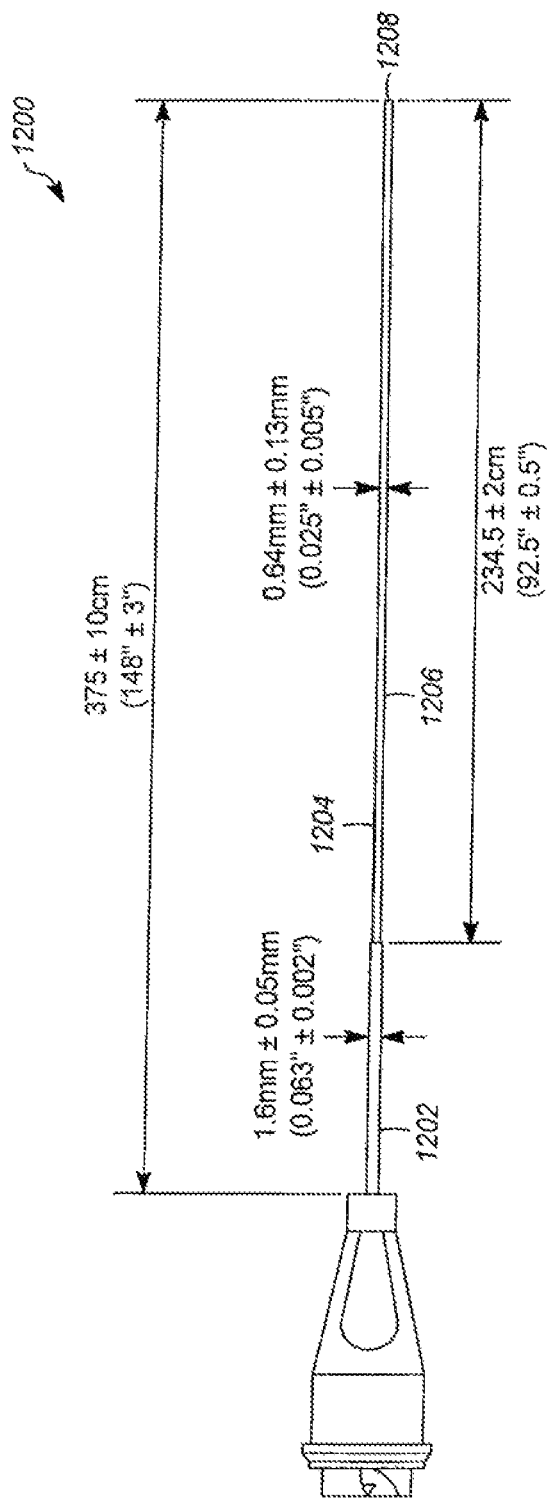
FIG. 12 is a side view of a reinforced EHL probe.
Figure 13A:
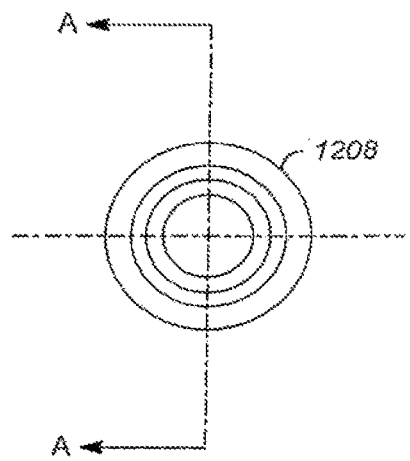
FIGS. 13*a*, 13*b*, 13*c*, and 13*d* illustrate enlarged views of a rounded tip of an EHL probe.
Figure 13B:
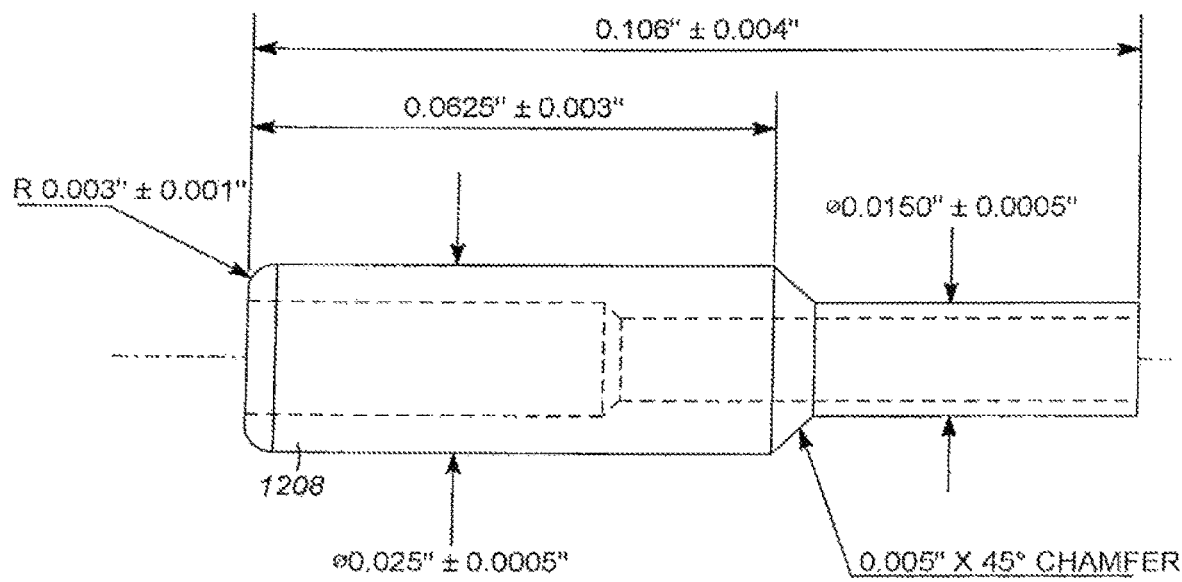
Figure 13C:
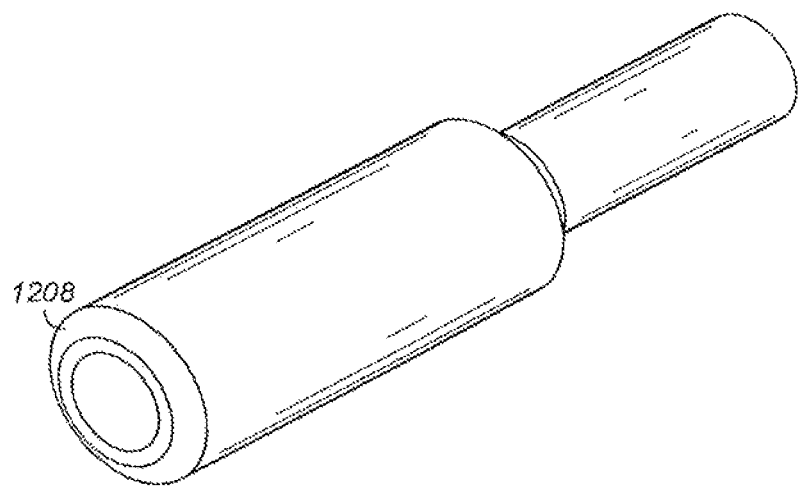
Figure 13D:
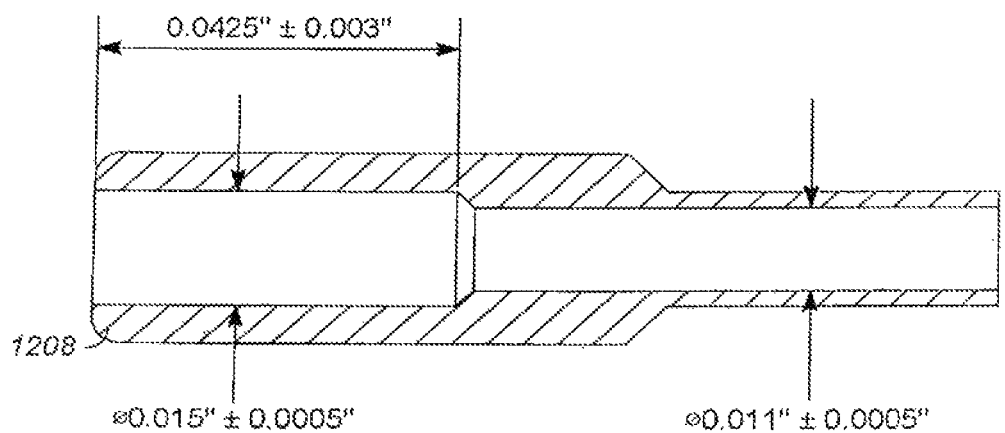

FIG. 12 is a side view of a reinforced EHL probe 1200. In one implementation, the linear strength of an EHL probe 1200 is improved by placing a stiffening over-sheath 1202 partially over the EHL probe 1200. The stiffening over-sheath 1202 may be constructed of materials such as Kynar®, Pebax®, or other similar materials.

In another implementation, the linear strength of an EHL probe 1200 is improved by using non-kinking formulations of a polyimide sheath material, such as those with thicker insulation, or ribbed or ringed areas along a length of a sheath or insulating material 1204. Examples of these types of materials are provided by Micro Lumen.

In yet other implementations, the linear strength of an EHL probe 1200 is improved by using an outer sheath 1204 of a polyimide sheath/insulation either coated or impregnated with lubricious materials such as Teflon or hydrophilic coatings. The more lubricious surface of the EHL probe would reduce a linear friction of the EHL probe as it is inserted through long channels.

In another implementation, the linear strength of an EHL probe 1200 is improved by using conductor wire 1206 of special manufacture, such as stainless steel wire with copper coating. The stainless steel center would provide greater stiffness for push strength, and the copper coating would provide for a less resistive current path. Because EHL probes 1200 are often used in a radio frequency (RF) range, and RF currents tend to flow at the surface of a wire rather than at the core of the wire, the added resistance of the stainless steel wire would not significantly affect the EHL probe 1200 performance.

In some embodiments, one or more of the implementations described above for improving the linear strength of the EHL probe 1200 may increase the linear strength of the EHL probe 1200 by approximately 50%.

In yet another implementation, an EHL probe 1200 is constructed to allow for insertion into long channels by rounding a tip 1208 of the EHL probe 1200 as shown in FIGS. 13*a*, 13*b*, 13*c*, and 13*d*. By rounding the tip 1208 of the EHL probe 1200, the tip 1208 of the EHL probe 1202 would be more likely to slide and prevent the tip 1208 of the EHL probe 1202 from "digging" into tissue, or a sheath or a scope.

Electrical sources such as those described above with respect to FIGS. 1-13 may use spark gap technology. The gaps used in spark gap technology may be sealed, noble gas spark discharge tubes that have an approximate life of approximately 400,000 to 500,000 discharges. After approximately 400,000 to 500,000 discharges, the gaps can no longer "break over" at a proper voltage.

An electrical source used with an EHL probe may record information such as a number of times a gap fires an EHL probe, a power of a gap when the gap files an EHL probe, a frequency of a gap firing an EHL probe, a unique identifier provided by an EHL probe, or any other information that may be useful to the electrical source in determining a remaining number of times a gap may fire an EHL probe. When the electrical source determines that a gap may no longer be able to file an EHL probe, the electrical source may display a warning message indicating that maintenance or replacement of the gap is necessary.

In some implementations, the electrical source may include an internal power source such as a battery so that when external power is not provided to the electrical source, the electrical source is able to maintain the recorded information regarding the gap. Additionally, in some implementations, the electrical source may communicate with a computer so that the computer may retrieve the recorded information stored at the electrical source for purposes of record keeping, performance analysis, or trouble shooting of the electrical source and/or an EHL probe.

It is intended that the foregoing detailed description be regarded as illustrative rather than limiting, and that it be understood that it is the following claims, including all equivalents, that are intended to define the spirit and scope of this invention.

The invention claimed is:

1. An invasive electrohydraulic lithotripter probe comprising:
    an invasive electrohydraulic lithotripter tip comprising:
        a first cylindrical electrode; and
        a second cylindrical electrode coaxially aligned with the first cylindrical electrode, wherein at least a portion of the second cylindrical electrode is positioned within an interior of the first cylindrical electrode;
    wherein the invasive electrohydraulic lithotripter probe is dimensioned and configured to be threaded through a human vein or artery of a patient and delivered to a position within an interior of the human vein or artery adjacent to concretions within the interior of the human vein or artery; and
    wherein the first and second cylindrical electrodes are positioned on the invasive electrohydraulic lithotripter tip such that when the first and second cylindrical electrodes are charged at different polarities, an electric arc between the first and second cylindrical electrodes causes a shockwave within a liquid to radiate radially in a direction that is transverse from a longitudinal axis of the invasive electrohydraulic lithotripter probe, such that while the invasive electrohydraulic lithotripter probe is positioned within an interior of the human vein or artery adjacent to concretions, the invasive electrohydraulic lithotripter probe is configured to break up the concretions positioned adjacent to the invasive electrohydraulic lithotripter tip in a location substantially transverse to the longitudinal axis of the invasive lithotripter probe.

2. The invasive electrohydraulic lithotripter probe of claim 1, further comprising:
    a flexible encapsulating member surrounding at least a portion of the invasive electrohydraulic lithotripter tip, where the flexible encapsulating member is configured to encapsulate a liquid.

3. The invasive electrohydraulic lithotripter probe of claim 1, wherein at least a portion of a distal edge of the invasive electrohydraulic lithotripter tip is a rounded bevel.

4. The invasive electrohydraulic lithotripter probe of claim 1, further comprising:
    a stiffening over-sheath positioned over at least a part of insulating material of the invasive electrohydraulic lithotripter probe, the stiffening over-sheath configured to reinforce a linear strength of at a least a portion of the invasive electrohydraulic lithotripter probe by up to approximately 50%.

5. The invasive electrohydraulic lithotripter probe of claim 4, wherein the stiffening over-sheath defines at least one ribbed area or ringed area that is configured to reduce kinking of the invasive electrohydraulic lithotripter probe.

6. The invasive electrohydraulic lithotripter probe of claim 1, wherein the invasive electrohydraulic lithotripter probe comprises polyimide that further reinforces the linear strength of the invasive electrohydraulic lithotripter probe.

7. The invasive electrohydraulic lithotripter probe of claim 1, wherein the invasive electrohydraulic lithotripter probe comprises a polyimide sheath impregnated with a lubricous material that further reinforces the linear strength of the invasive electrohydraulic lithotripter probe.

8. The invasive electrohydraulic lithotripter probe of claim 1, where the invasive electrohydraulic lithotripter tip has a length in excess of 250 cm.

9. The invasive electrohydraulic lithotripter probe of claim 1, wherein the invasive electrohydraulic lithotripter probe is in communication with an electrical source configured to charge the first cylindrical electrode to a first polarity.

10. The invasive electrohydraulic lithotripter probe of claim 9, wherein the electrical source comprises an electrohydraulic generator.

* * * * *